(12) United States Patent
Bayliff et al.

(10) Patent No.: US 9,932,622 B2
(45) Date of Patent: Apr. 3, 2018

(54) WOUND PROGNOSIS

(75) Inventors: Simon William Bayliff, Yorkshire (GB); Breda Mary Cullen, Yorkshire (GB); Molly Gibson, Yorkshire (GB)

(73) Assignee: Woundchek Laboratories B.V., Amsterdamn (NL)

( * ) Notice: Subject to any disclaimer, the term of this patent is extended or adjusted under 35 U.S.C. 154(b) by 0 days.

(21) Appl. No.: 13/982,913

(22) PCT Filed: Jan. 31, 2012

(86) PCT No.: PCT/GB2012/050199
§ 371 (c)(1),
(2), (4) Date: Oct. 22, 2013

(87) PCT Pub. No.: WO2012/104620
PCT Pub. Date: Aug. 9, 2012

(65) Prior Publication Data
US 2014/0045761 A1 Feb. 13, 2014

(30) Foreign Application Priority Data

Jan. 31, 2011 (GB) .................................. 1101663.1
Sep. 23, 2011 (GB) .................................. 1116523.0
Oct. 20, 2011 (GB) .................................. 1118119.5

(51) Int. Cl.
| | |
|---|---|
| *A61K 38/39* | (2006.01) |
| *A61K 47/48* | (2006.01) |
| *A01N 43/04* | (2006.01) |
| *A61K 31/715* | (2006.01) |
| *C12Q 1/37* | (2006.01) |
| *C12M 1/34* | (2006.01) |
| *C12M 3/00* | (2006.01) |
| *C40B 30/08* | (2006.01) |
| *G01N 33/573* | (2006.01) |
| *G01N 33/68* | (2006.01) |

(52) U.S. Cl.
CPC ............ *C12Q 1/37* (2013.01); *G01N 33/573* (2013.01); *G01N 33/6893* (2013.01); *G01N 2800/20* (2013.01)

(58) Field of Classification Search
None
See application file for complete search history.

(56) References Cited

U.S. PATENT DOCUMENTS

| | | | | |
|---|---|---|---|---|
| 4,897,444 A | * | 1/1990 | Brynes ..................... | C12Q 1/37 435/23 |
| 5,266,266 A | | 11/1993 | Nason | |
| 5,770,229 A | | 6/1998 | Tanihara | |
| 2003/0119073 A1 | * | 6/2003 | Quirk ..................... | C12Q 1/37 435/7.4 |
| 2007/0298121 A1 | | 12/2007 | Monroe | |
| 2008/0176262 A1 | | 7/2008 | Kaplan | |

FOREIGN PATENT DOCUMENTS

| | | | | |
|---|---|---|---|---|
| EP | 1536845 | | 9/2003 | |
| EP | 1153622 | | 10/2004 | |
| GB | EP 0318318 A1 | * | 5/1989 | ............... C12Q 1/37 |
| GB | 2381452 A | | 5/2003 | |
| GB | WO 03/040406 | * | 5/2003 | |
| GB | 2393120 | | 3/2004 | |
| GB | 2411230 | | 8/2005 | |
| GB | 2411231 | | 8/2005 | |
| GB | 2418145 | | 3/2006 | |
| GB | 2422664 | | 8/2006 | |
| GB | CA 2648712 A1 | * | 11/2007 | ............... C12Q 1/37 |
| GB | 2435790 B | | 12/2009 | |
| GB | 2487729 | | 8/2012 | |
| WO | 98/00180 | | 1/1998 | |
| WO | 03/040406 | | 5/2003 | |
| WO | WO 2003/040406 | * | 5/2003 | |
| WO | 03/058237 | | 7/2003 | |
| WO | 03/063693 | | 8/2003 | |
| WO | 04/024197 | | 3/2004 | |
| WO | 04/026200 | | 4/2004 | |
| WO | 05/021780 | | 3/2005 | |
| WO | 06/03023 | | 3/2006 | |
| WO | 2006/030232 A2 | | 3/2006 | |
| WO | 06/079826 | | 8/2006 | |

(Continued)

OTHER PUBLICATIONS

Tarlton et al., Wound Repair and Regeneration, 1999, 7(5), 347-55.*
Neumann et al. "Characterization of Mca-Lys-Pro-Leu-Gly-Leu-Dpa-Ala-Arg-NH2, a fluorogenic substrate with increased specificity constants for collagenases and tumor necrosis factor converting enzyme" Analytical Biochemistry 328:166-173. Published 2004.*
Cullen, "A comparison of collagen containing wound dressings to modify the chronic wound environment", Would Repair and Regeneration, 15(6):A148 (2007).
Liu et al., "Increased Matrix Metalloproteinase-9 Predicts Poor Wound Healing in Diabetic Foot Ulcers", Diabetes Care, 32(1):117-119, (2009).
Muller et al., "Matrix metalloproteinases and diabetic foot ulcers: the ration of MMP-1 to TIMP-1 is a predictor of wound healing", Diabetic Medicine, 25(4):419-426, (2008).

(Continued)

*Primary Examiner* — James H Alstrum-Acevedo
*Assistant Examiner* — Zachary J Miknis
(74) *Attorney, Agent, or Firm* — McDonnell Boehnen Hulbert & Berghoff LLP

(57) ABSTRACT

Methods and devices for determining the healing status of wounds, in particular of chronic wounds are provided. Also provided are kits comprising the diagnostic devices, and methods of wound diagnosis and treatment using the diagnostic devices and methods. A diagnostic apparatus (device) for monitoring wounds that exude a wound fluid and determining whether said wounds would be responsive to treatment with wound therapy such as oxidized cellulose therapy is also provided along with kits comprising the diagnostic apparatus and a wound dressing. Furthermore, methods of prognosing and treating wounds that exude a wound fluid are also provided.

15 Claims, 20 Drawing Sheets

(56) References Cited

FOREIGN PATENT DOCUMENTS

| WO | 07/128980 | 11/2007 |
| WO | 08/070865 | 6/2008 |
| WO | 09/024805 | 2/2009 |
| WO | 09/063208 | 5/2009 |
| WO | 10/022281 A1 | 2/2010 |
| WO | 10/151878 A2 | 12/2010 |
| WO | 12/104620 | 8/2012 |

OTHER PUBLICATIONS

Neumann et al., "Characterization of Mca-Lys-Pro-Leu-Gly-Leu-Dpa-Ala-Arg-NH2, a fluorogenic substrate with increased specificity constants for collagenases and tumor necrosis factor converting enzyme", Analytical Biochemistry, 328:166-173 (2004).

Ozcaka et al., "Smoking and matrix metalloproteinases, neutrophil elastase and myeloperoxidase in chronic periodontitis", Oral Diseases, 17(1):68-76 (2011).

Patrick et al., "Hydrogels for the Detection and Management of Protease Levels", Macromolecular Bioscience, 10(10):1184-1193 (2010).

Rao et al., "a1-Antitrypsin in Degraded and Non-Functional in Chronic Wounds but Intact and Functional in Acute Wounds: The Inhibitor Protects Fibronectin from Degradation by Chronic Wound Fluid Enzymes", Journal of Investigative Dermatology, 105(572-578), 1995.

Smeets et al., "Effect of oxidised regenerated cellulose/collagen matrix on proteases in wound exudate of patients with chronic venous ulceration", International Wound Journal, 5(2):195-203, (2008).

Tarlton et al, "Postsurgical wound progression monitored by temporal changes in the expression of matrix metalloproteinase-9", British Journal of Dermatology, 137(4):506-516, (1997).

Tarlton et al., "Prognostic value of markers of collagen remodeling in venous ulcers", Wound Repair and Regeneration, 7(5):347-355 (1999).

Wiegand et al., "Protease and pro-inflammatory cytokine concentrations are elevated in chronic compared to acute wounds and can be modulated by collagen type I in vitro", Archives of Dermatological Research, 302(6):419-428 (2010).

Fagerstam et al., "Immunochemistry", p. 949-970 (1994).

Cullen et al., "Mechanism of action of PROMOGRAN, a protease modulating matrix, for the treatment of diabetic foot ulcers", Wound Repair and Regeneration, 10(1):16-25 (2002).

Eming et al., "Differential Proteomic Analysis Distinguishes Tissue Repair Biomarker Signatures in Wound Exudates Obtained from Normal Healing and Chronic Wounds", Journal of Proteome Research, 9:4758-4766 (2010).

Rayment et al., "Increased matrix metalloproteinase-9 (MMP-9) activity observed in chronic wound fluid is related to the clinicial severity of the ulcer", Br. J. Dermatol., 158:951-961 (2008).

Reiss et al., "Matrix Metalloproteinase-9 Delays Wound Healing in a Murine Wound Model", Surgery, 147(2):295-302 (2010).

Utz et al., "Metalloproteinase Expression is Associated with Traumatic Wound Failure", Journal of Surgical Research, 159:633-639 (2010).

Krisp et al., "Proteome analysis reveals antiangiogenic environments in chronic wounds of diabetes mellitus type 2 patients", Proteomics, 13:2670-2681 (2013).

\* cited by examiner

Boxplot of Percent Reduction in Healing and Non Healing Leg Ulcers

Boxplot of Percent Reduction in Healing and Non Healing Pressure Ulcers

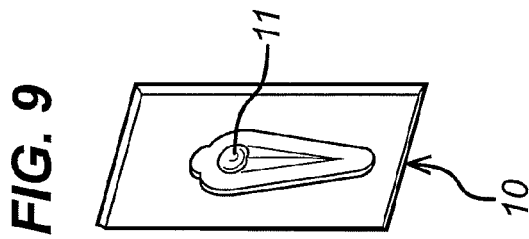
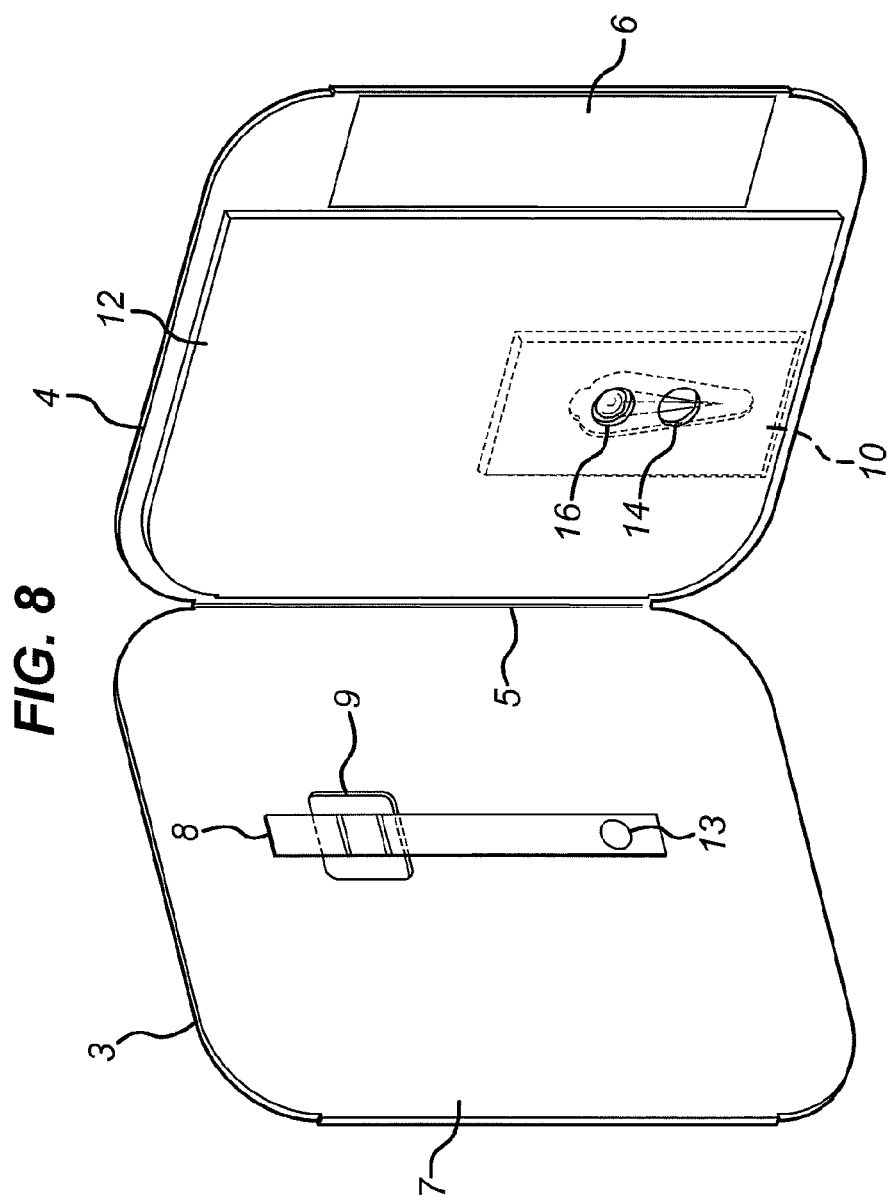

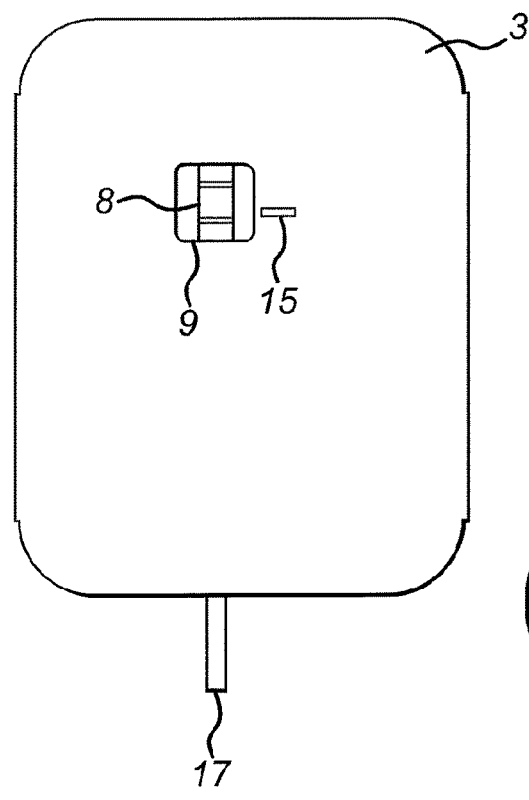
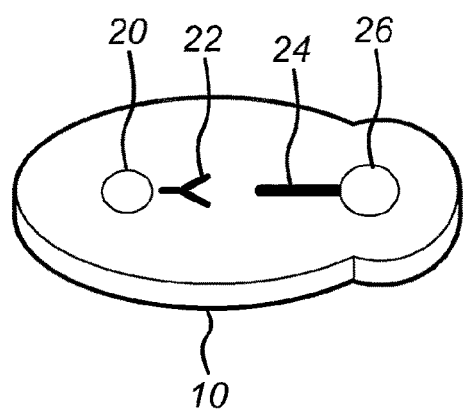
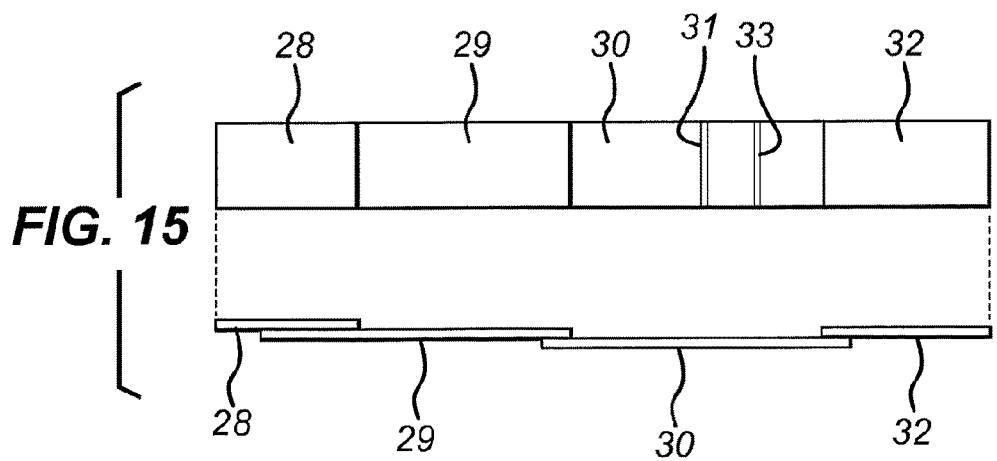

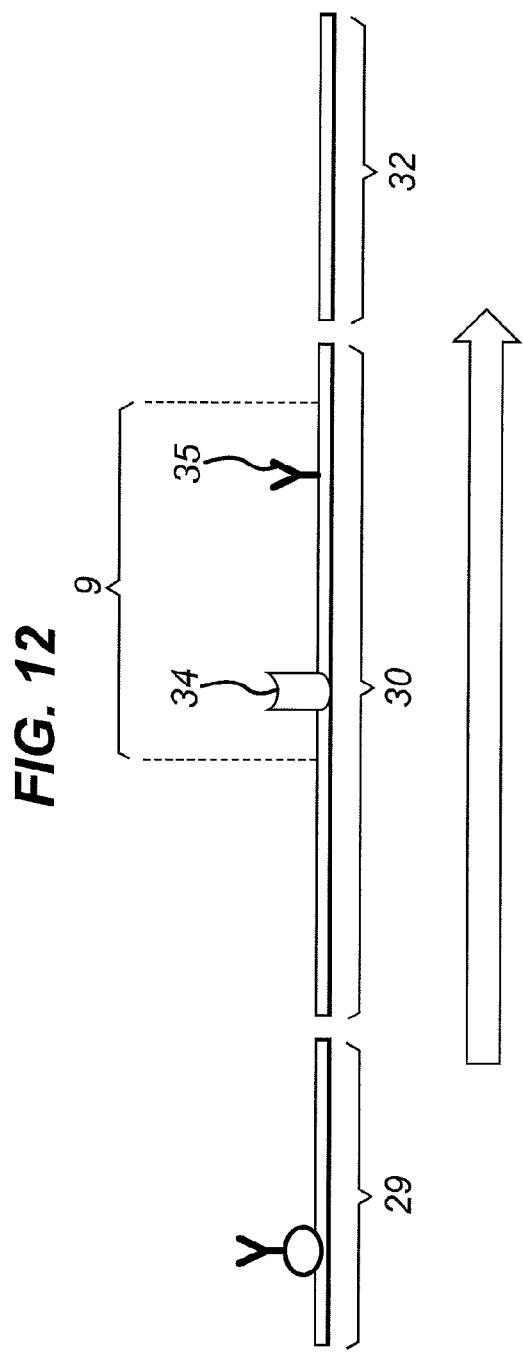

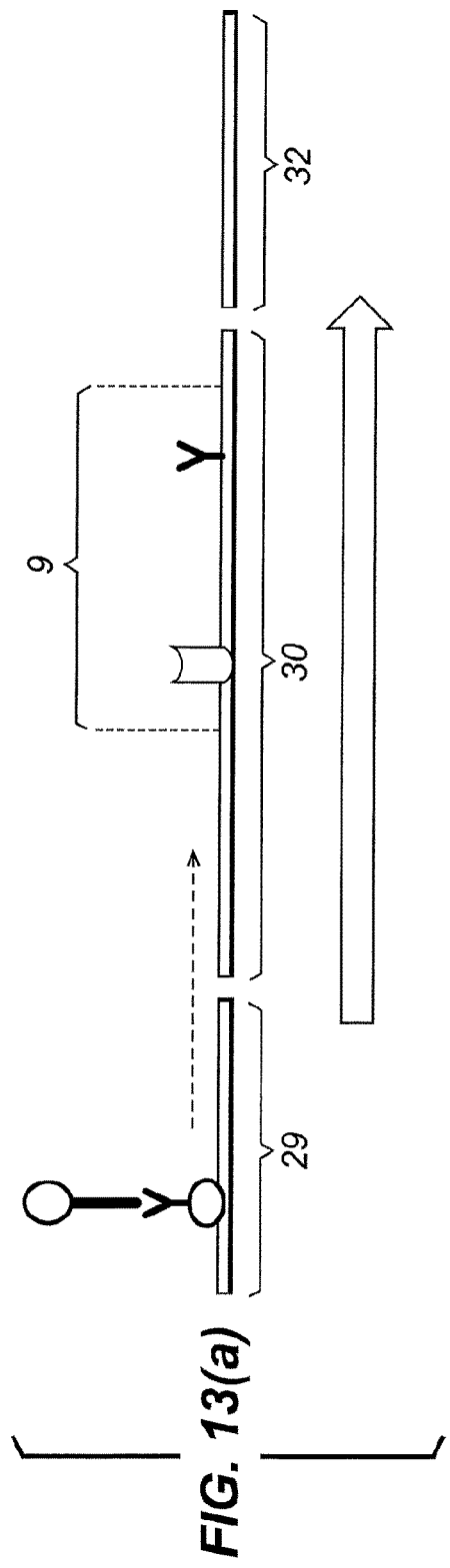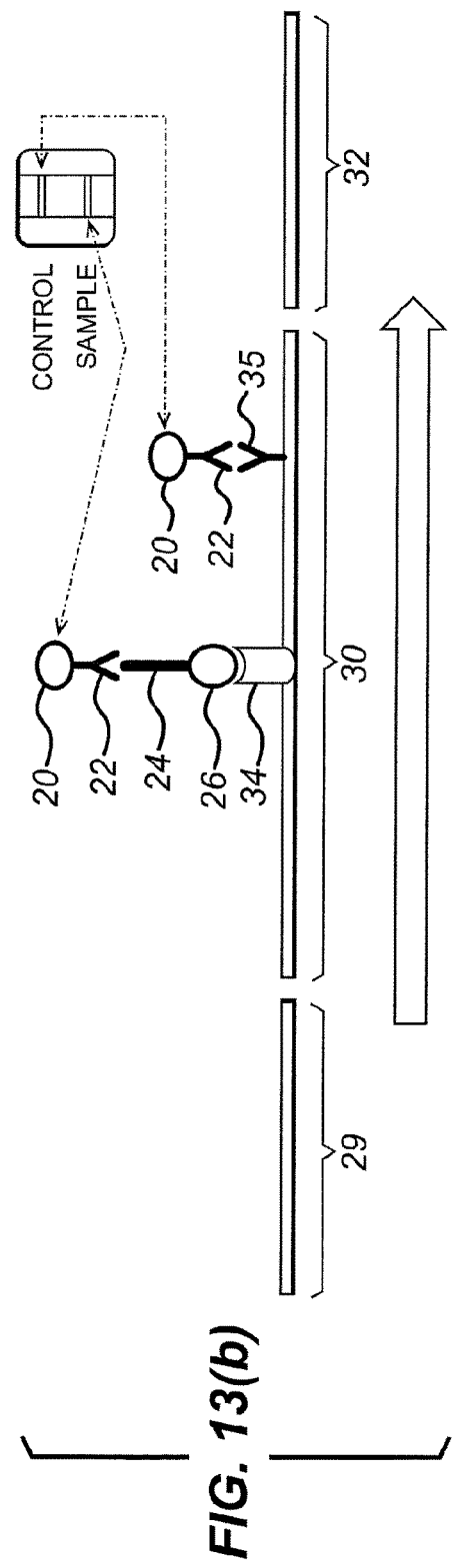
FIG. 13(a)
FIG. 13(b)

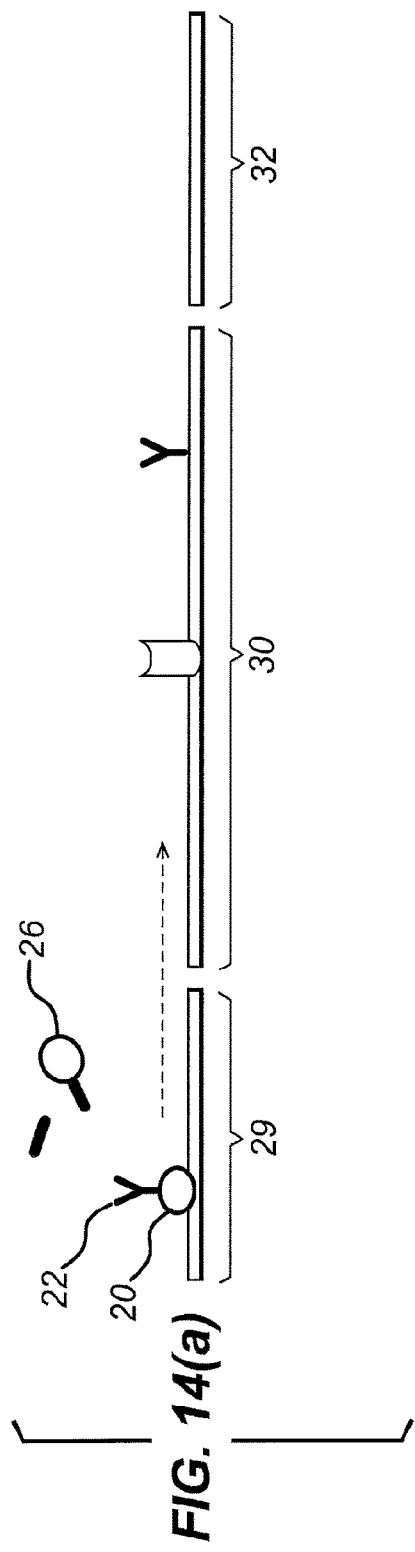
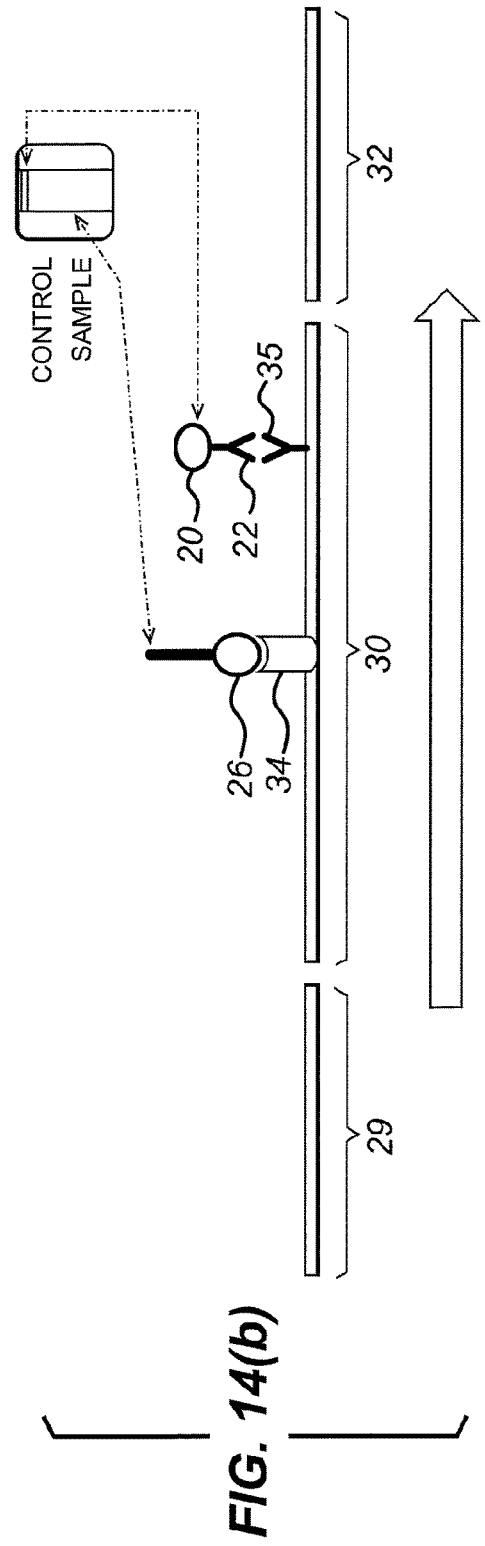
FIG. 14(a)
FIG. 14(b)

Boxplot of Week 0

Boxplot of MMP 1

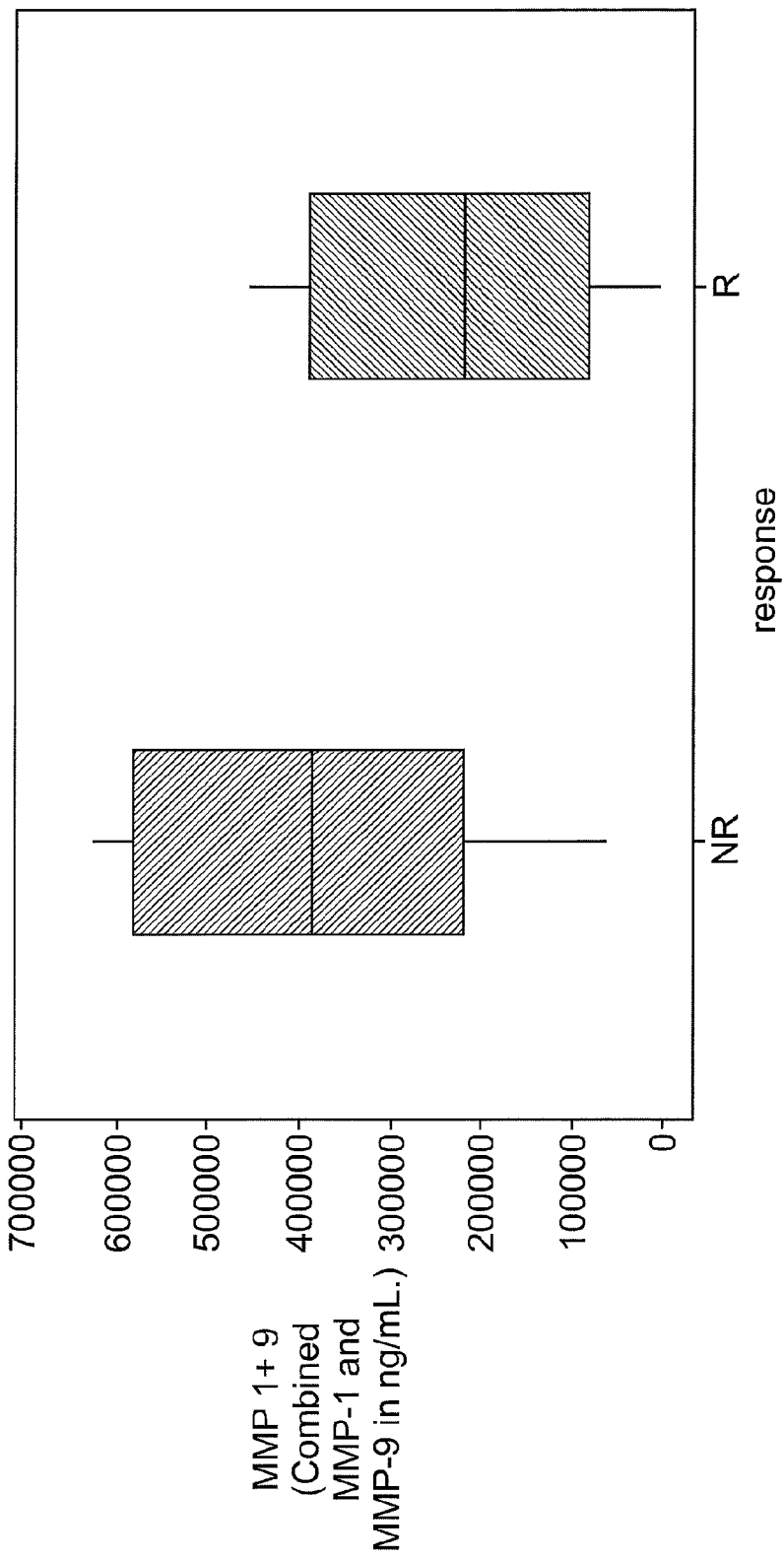

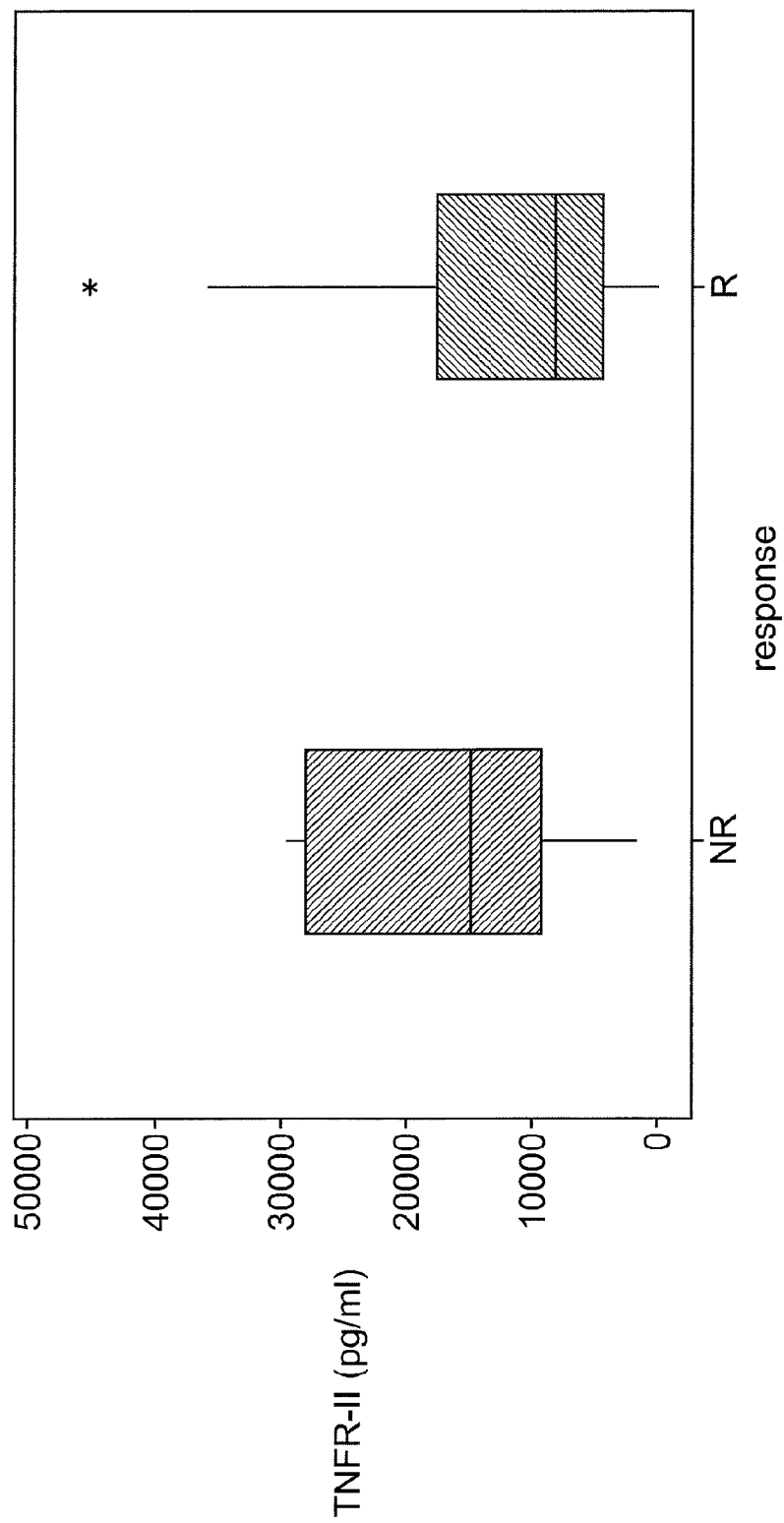

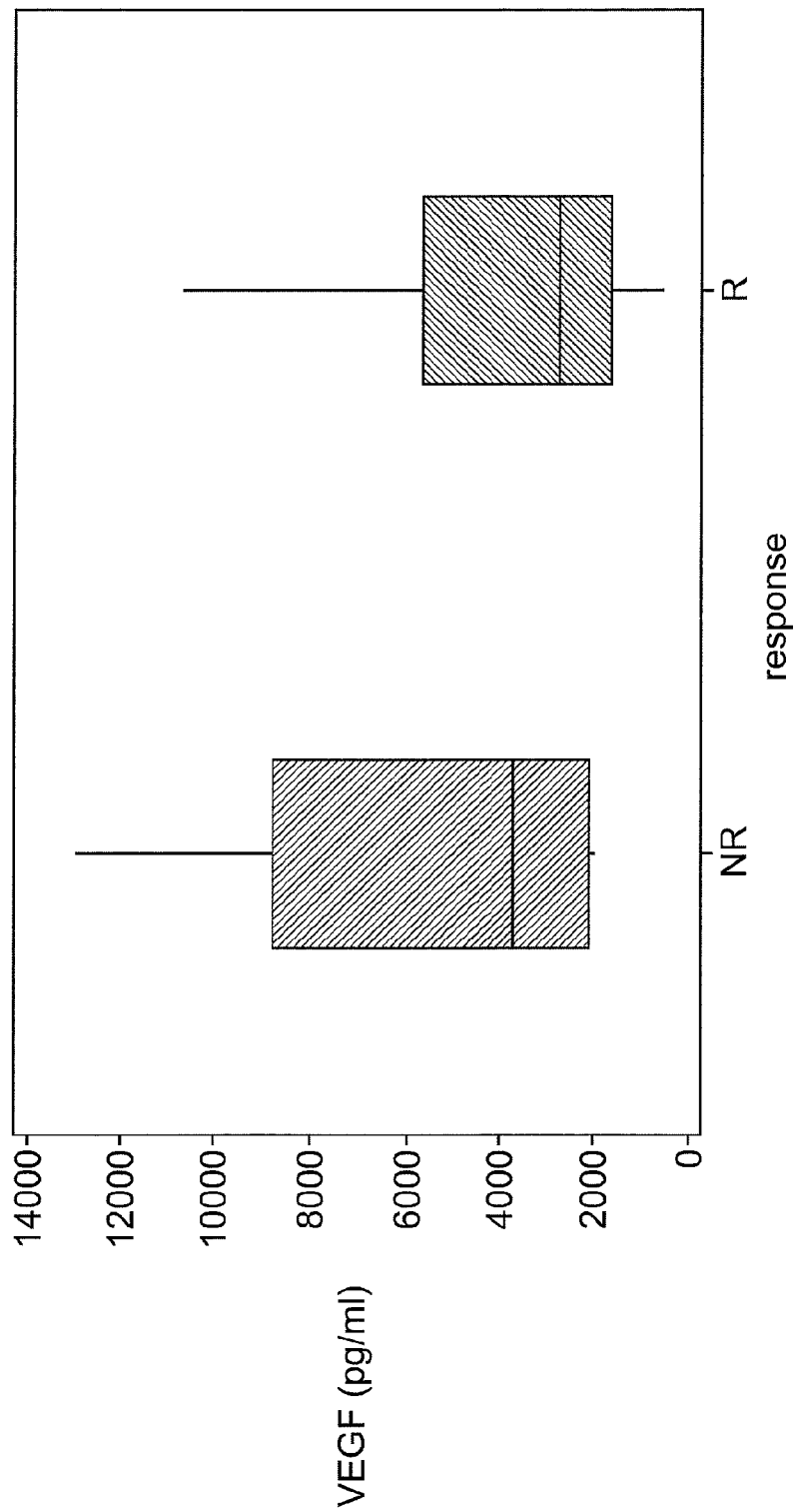

WOUND PROGNOSIS

REFERENCE TO A "SEQUENCE LISTING"

The sequence listing submitted via EFS-Web, in compliance with 37 CFR § 1.52(e)(5), is incorporated herein by reference. The sequence listing text file submitted via EFS-Web contains the file "98282-127_ST25", created on Jul. 31, 2013, which is 4 KB in size.

TECHNICAL FIELD

The present invention relates to methods and devices for determining the healing status of wounds, in particular of chronic wounds. Also provided are kits comprising the diagnostic devices, and methods of wound diagnosis and treatment using the diagnostic devices and methods. The present invention also relates to an apparatus for monitoring the status of wounds. The invention also provides a method of treating a wound that exudes a wound fluid and a method of prognosing a wound that exudes a wound fluid. Diagnostic apparatus and kits comprising a diagnostic apparatus and a wound dressing are also provided for use in the methods of the invention.

The word 'chronic' is a generic term used to describe a condition that is 'of long duration' or that 'recurs frequently'. It is for this reason it is used to describe wounds that are difficult to heal and usually persist for a long period of time. Thus, while all wounds have the potential to become chronic, traditionally chronic wounds are identified by their underlying aetiology such as venous insufficiency, arterial perfusion, diabetes, or unrelieved pressure as well as systemic factors such as nutritional status, immunosuppression, and infection all of which may contribute to poor wound healing. In general it is accepted that acute wounds follows an orderly sequence of events and typically heal within 2-4 weeks, whereas a chronic wound is thought to be stuck in the inflammatory phase of healing and can therefore persist for months or even years. Chronic wounds have been shown to contain elevated levels of inflammatory cytokines, free radicals and proteases which create a hostile wound environment, detrimental to healing.

Predicting the healing status of a chronic wound is difficult, and is often complicated by the number of risk factors associated with these wounds. The most commonly used objective measure is a reduction of the ulcer surface area. This was ratified by The European Wound Management Association whom produced a review of the different outcome measures used in controlled and comparative wound healing studies. In this study, they reported that the most frequently used outcome was wound surface area reduction and that this was a valid end point for such studies. It has been shown that a reduction in wound area after two to four weeks is a good predictor of the wound's ability to heal by week twelve. It is harder to determine from the literature the exact percentage reduction which should be used to predict healing status however it is generally accepted that for venous leg ulcers a 20-40% reduction in wound area within 2-4 weeks is predictive of healing, whereas for diabetic foot ulcers a reduction of 50% within the first 4 weeks is predictive of healing.

It would be desirable to be able to determine whether a chronic wound is healing, or not, by means of a simple test that does not depend on the measurement of wound surface area over a period of two to four weeks. Such a test would enable the appropriate therapy to be selected as early as possible during wound treatment. If the wound is non-healing, then special dressings or other therapies can be used as early as possible and/or an ineffective therapy can be changed. If the wound is found to be healing without special intervention, then the additional expense of special therapies can be avoided.

It would also be desirable to be able to determine whether a patient will respond to a particular wound treatment.

BACKGROUND ART

Many documents describe the measurement of various different analytes in chronic and acute wound fluid. The following documents describe the measurement of endogenous protease enzymes in wound fluid.

C. N. Rao et al. in the *Journal of Investigative Dermatology*, vol. 105(4), pages 572-578 (1995) describe the results of analysing chronic and acute wound fluids for elastase, alpha-1-antitrypsin (AAT) and fibronectin. It was found that the elastase level was 10 to 40 times higher in the chronic wound fluid.

US-A-2003/0119073 describes sensors for the assay of catabolic protease enzymes in wound fluid. The analyte enzymes include human neutrophil elastase (hNE). It is suggested therein that the invention can be used in a method of treating chronic wounds by detecting the presence of catabolic protease enzymes, and then treating the wound with inhibitors that are specific for the detected enzymes.

WO 2006/030232 describes a diagnostic test apparatus for determining a ratio of: (a) at least one endogenous protease enzyme inhibitor, to (b) at least one endogenous protease enzyme, in a sample of a wound fluid. The apparatus is used in a method of treating a wound, and used for identifying wounds that are likely to respond well to treatment with oxidized regenerated cellulose (ORC) containing dressings. For example, the apparatus is used for identifying prospective responders and non-responders to treatment of wounds with PROMOGRAN™ collagen/ORC wound dressing.

John F. Tarlton et al. in Wound Repair and Regeneration, Vol. 7(5), pages 347-355 (1999) describe an academic study into the prognostic value of markers of collagen remodelling in venous ulcers. The following markers were studied: proMMP-2, proMMP-9, neutrophil elastase (hNE), MMP-2 and MMP-9. The data showed that expression of MMPs-2 and 9 and hNE were higher in venous ulcer exudates than in acute wound fluids. Also studied was a comparison of the above markers in healing versus non-healing ulcers. A further study was performed in which wound fluids were compared from healing and non-healing regions of the same ulcer in order to eliminate patient-to-patient variation. The data showed only very weak correlation, if any, of MMP-2 and MMP-9 to wound healing status in the multiple-patient study. The correlation for neutrophil elastase was also quite weak. However, the comparison experiments done on wound fluids from different regions of the same wound did show a statistically significant correlation of neutrophil elastase to wound healing status, and a weakly statistically significant correlation of MMP-9 to wound healing status.

Alison G. Patrick et al. in Macromolecular Bioscience, Vol. 10, pages 1184-1193 (2010) describe hydrogel particles having surface bonded moieties for the detection of elastase, MMP-1 and/or MMP-12. The moieties consist of an enzyme-specific peptide substrate linking two FRET chromophores, whereby cleavage of the peptide results in a fluorescence signal. The peptides are selective for elastase, or for MMP-1 and MMP-12. It is mentioned that MMPs are associated with the progression of chronic wounds.

Ralf Smeets et al. in International Wound Journal, Vol. 5(2), pages 195-203 (2008) describe the effect of collagen/ORC sponge dressing treatment on "gelatinase activity", and also on levels of MMP-2, and elastase in chronic wounds. The results show that collagen/ORC does not significantly effect the MMP-2 level, but that it significantly reduces the gelatinase and elastase activities.

Cornelia Wiegand et al. in Archives of Dermatological Research, Vol. 302, pages 419-428 (2010) describe measurement of various proteases in acute chronic wound fluids. The measured proteases were neutrophil elastase, MMP-2 and MMP-13. These were all found to be elevated in chronic wounds relative to acute wounds. Levels of these proteases were found to decrease in the course of wound healing.

Breda Cullen et al. in Wound Repair and Regeneration, Vol. 15 (6) page A148 (2007) describe a comparison of collagen/ORC/silver dressings with other collagen (+silver) dressings in the treatment of chronic wounds. The results demonstrate that while the collagen containing dressings could remove MMP-type proteases, not all inactivate elastase. However, the collagen/ORC/silver dressings significantly reduced the levels of both elastase and total MMP.

WO-A-03058237 describes sensors for detection of various protease enzymes in wound fluid. The analytes include MMP-1, MMP-8. MMP-9 and neutrophil elastase, either singly or simultaneously. The specification also suggests then treating the wound with inhibitors that are specific for protease enzymes found in the wound. The sensors described in the specification are all immunological.

GB-A-2422664 refers to measurement of various analytes, including MMP-1, MMP-8, MMP-9 and neutrophil elastase in wound fluid. Peptide sequences are disclosed that are cleavable by elastase, MMP-2 or MMP-9. Also disclosed are devices with multiple lateral flow paths for measuring multiple analytes.

WO-A-2008070865 describes methods for evaluating the status of the healing process of a wound comprising contacting wound fluid with a cleavable peptide. The method may be used to detect at least one protease selected from the group of MMP-2, MMP-8, MMP-9 and elastase.

WO98/00180 and EP-A-1153622 describe the use of freeze-dried sponges comprising oxidized regenerated cellulose (ORC), optionally admixed with collagen, for the treatment of chronic wounds. Dressings based on oxidized cellulose have been found to give outstanding results in the treatment of chronic wounds, including diabetic ulcers, venous ulcers and decubitis ulcers.

WO 2004/024197 and EP-A-1536845 describe the use of wound dressing materials comprising complexes of anionic polysaccharides with silver. In particular, wound dressing materials comprising complexes formed between anionic polysaccharides, such as ORC, and silver, and to the uses thereof for the treatment of wounds are disclosed.

GB-A-2393120 describes the use of wound dressings based on ORC in combination with chitosan for the treatment of chronic wounds. The dressings are shown to reduce the levels of elastase and collagenase in the wound fluids.

It will be apparent from the foregoing that levels of matrix metalloproteinases and human neutrophil elastase levels are thought to be elevated in chronic wound fluid relative to acute wound fluid. Changes in the levels of these markers may be correlated to wound healing. However, the above references do not show how to use these markers to distinguish between healing and non-healing chronic wounds. For example, Tarlton et al. found little or no statistically significant correlation between these markers and healing/non-healing chronic wound type in inter-patient studies. Furthermore, protease levels in any sample of wound fluid appear to be poorly correlated. Thus, a wound having high levels of hNE may not also have elevated levels of MMP. This may be due to interactions between proteases. For example hNE acts as a physiological activator of MMPs including MMP-9 which is synthesised in a latent, inactive form. Additionally, there is some biochemical redundancy between the proteases; although some proteases are more efficient than others there is a crossover and synergy of substrates between these proteases, for example elastin can be degraded by both MMP-9 and Elastase, and both MMP-8 and MMP-9 are required to digest Collagen type I. Therefore it may be possible for a non-healing wound to be low in one protease but this could be compensated by an excess of another protease.

Thus, it is an object of the present invention to provide improved means to distinguish healing from non-healing chronic wounds. It is a further object to provide such a means that can be performed on a sample of wound fluid removed from the wound. It is a further object to provide a method that requires only a measurement made at a single point in time, in contrast to the measurement of wound area, which requires multiple measurements over an extended period. It is a further object of the invention to avoid unnecessary special therapy on other patients who present with healing wounds. Preferably, the present invention seeks to identify a sub-group of patients wherein the probability of their wound being non-healing is at least about 80%, suitably at least about 90%.

It has also been found that a sub-group of chronic wound patients exhibit a particularly large improvement in wound healing when treated with collagen/ORC sponges.

Thus, it is also an object of the present invention to provide alternative or improved means to identify as early as possible the sub-group of patients that exhibit a particularly large improvement in wound healing when treated with oxidized cellulose so that they can receive maximum benefit from this therapy. It is a further object of the invention to avoid unnecessary oxidized cellulose therapy on other patients who may be less likely to benefit. Accordingly, it is an object of the present invention to identify which patients would be more likely to respond to treatment with oxidised cellulose before treatment with oxidised cellulose has begun

DISCLOSURE OF THE INVENTION

The present inventors have found that non-healing wounds can be distinguished from healing wounds by measuring both human neutrophil elastase (hNE) activity and the activity of at least one matrix metalloproteinase (MMP) in a sample of the wound fluid, and comparing these measured values with threshold values indicative of non-healing wounds. The measurement of both analyte types compensates for inter-patient variations in the individual analytes and thereby reduces false negative results. The selection of a sufficiently high threshold reduces false positive results. Overall, at least 80% or 90% of the wounds giving a positive result in this test are found to be non-healing.

Accordingly, in a first aspect, the present invention provides a method of wound prognosis comprising the steps of: measuring the level of human neutrophil elastase (hNE) in a sample of wound fluid from a wound; measuring the level of at least one matrix metalloproteinase (MMP) in a sample of wound fluid from said wound; and assigning said wound to a non-healing category if either said level of hNE exceeds a first predetermined threshold or said level of MMP exceeds a second predetermined threshold. The measurement of hNE and one or more MMPs may be carried out simultaneously or sequentially in one or more diagnostic devices. It will be seen below that in certain embodiments a single measurement is used to determine a sum or weighted average of hNE and one or more MMP levels.

In a second aspect the present invention provides a device for simultaneously or sequentially measuring the levels of hNE and of at least one MMP in a sample of wound fluid, and for providing a detectable output if either the level of the hNE exceeds a first predetermined threshold or the level of said at least one MMP exceeds a second predetermined threshold.

The term "level" may refer to the amount of the protease as determined by immunoassay, which may detect both active and inactive forms of the enzyme. More suitably, the term "level" refers to the activity of the protease, for example as determined by the rate of cleavage of a substrate for the protease.

The at least elastase and at least one matrix metalloproteinase are suitably endogenous proteases present in the chronic wound fluid.

In the above aspects or embodiments, the level of elastase may be indicated by total elastase-like activity, for example by measuring the rate of cleavage of a substrate for the hNE enzyme.

Suitably, the at least one matrix metalloproteinase includes MMPs selected from the group consisting of MMP-1, MMP-8, MMP-9 and MMP-12. Typically, the matrix metalloproteinases include MMP-1 and MMP-9. The level of more than one matrix metalloproteinase may be measured. In these embodiments, the relevant level for comparison with the threshold is the sum of the levels of the measured MMPs. In certain embodiments, the at least one matrix metalloproteinase is at least two matrix metalloproteinases. In certain embodiments, the at least one MMP is total MMP of all types in the sample. In certain embodiments, the level of at least one MMP is a weighted average (weighted sum) of the levels of more than one MMP.

The level of MMP may be determined by measuring the rate of cleavage of one or more substrates for the MMP enzymes. Certain peptide substrates are specific for one or more MMPs. As explained further below, certain peptide substrates are cleaved by more than one MMP. In these embodiments, the rate of cleavage may depend on the MMP, whereby the rate of cleavage is determined by the respective activities of the MMPs in the sample weighted by their respective reactivities with the substrate. The resulting weighted average (weighted sum) MMP activity is used as the measured level for comparison with a threshold value.

Likewise, in certain embodiments, a peptide substrate is cleaved both by hNE and by one or more MMPs. In these embodiments the rate of cleavage is determined by the respective activities of the hNE and the MMPs in the sample weighted by their respective reactivities with the substrate. The resulting weighted average (weighted sum) protease activity is used as the measured level for comparison with a threshold value to determine whether the wound is healing or non-healing.

Accordingly, in a third aspect the present invention provides a method of wound prognosis comprising the steps of: determining a weighted average (weighted sum) of the levels of human neutrophil elastase (hNE) and two or more matrix metalloproteinases (MMP); and assigning said wound to a non-healing category if said weighted average exceeds a threshold level.

In a fourth aspect, the present invention provides a device for use in a method of wound prognosis comprising the steps of: determining a weighted average (weighted sum) of the levels of human neutrophil elastase (hNE) and at least one matrix metalloproteinases (MMP); and assigning said wound to a non-healing category if said weighted average (weighted sum) exceeds a threshold value.

The weighted average (weighted sum) is suitably weighted by the respective reactivities of the hNE and MMPs with one or more cleavable substrates for these protease enzymes.

In embodiments of the present invention according to any aspect, the proteases determined include hNE, MMP-1 and MMP-9.

In embodiments, the selective reagent, such as a cleavable exogenous peptide substrate, is immobilized in the device, for example by chemical or physical bonding to a solid substrate in said device, as described in more detail below. In embodiments, the selective reagent is conjugated to an indicator moiety or a binding moiety to form a selective reagent-moiety conjugate that may or may not be bonded to a solid substrate in the measurement device of the invention.

Output signals may be of any suitable form as apparent to the skilled person. Suitable signals are disclosed herein. For example, output signals may be visual or auditory, and may be immediately recognisable (e.g. written text) or may require further interpretation by reference to a standard (e.g. a colour signal). In particular embodiments, the device is adapted to provide a visual output in the form of a colour line on a test strip, wherein the intensity of the colour line is indicative of the level of the protease analyte(s) in the sample.

It has also been found that the amounts of endogenous protease enzymes are particularly good predictors of the success of treatment with oxidized cellulose therapy. However, the measurement of individual marker analytes in samples of wound fluid, such as the measurement of individual endogenous protease enzymes has so far been unsuccessful in predicting whether wounds would be responsive to treatment with oxidized cellulose therapy before the treatment has commenced (see, e.g. FIGS. 19-23 and Reference Examples 2-6).

The present inventors have found, surprisingly, that the combined amount of elastases and matrix metalloproteinases in a sample of a wound fluid, whether before or during treatment with a protease inhibitor dressing, such as an oxidized cellulose dressing, correlates to the likelihood of (and rate of) healing by means of this therapy. In particular, it has been found, surprisingly, that the combined amount of elastase, MMP-1 and MMP-9 as determined from a sample of wound fluid is an especially good predictor of the success of treatment with oxidized cellulose therapy, In other words, whether a patient will be responsive or non-responsive to such treatment Accordingly, in a fifth aspect, the present invention provides a diagnostic apparatus for simultaneously or sequentially determining the amount of at least one elastase and at least one matrix metalloproteinase in a sample of a wound fluid wherein the amounts of protease inhibitors in the sample are not determined.

It will be appreciated that the concentration of more than one elastase and matrix metalloproteinase may be measured. In certain embodiments of the fifth aspect, the concentrations of at least two, three or four of these proteases are monitored. Typically, three of these proteases are measured.

In an embodiment of the fifth aspect, the at least one matrix metalloproteinase is at least two matrix metalloproteinases. Suitably, the at least one matrix metalloproteinase is selected from the group consisting of MMP-1, MMP-8, MMP-9 and MMP-12. Typically, the matrix metalloproteinases are MMP-1 and MMP-9.

In a sixth aspect, the invention provides a diagnostic apparatus for simultaneously or sequentially determining the amount of elastase, MMP-1 and MMP-9 in a sample of a wound fluid.

In the fifth and sixth aspects, or embodiments of these aspects, the amount of elastase may be indicated by total elastase-like activity. In some embodiments, the elastase may be selected from the group consisting of neutrophil elastase, latent elastase and/or active elastase. For example, the elastase may be neutrophil elastase. Typically, the elastase is active elastase.

For example, in one embodiment of the fifth or sixth aspects, the proteases determined are neutrophil elastase, MMP-1 and MMP-9.

In another embodiment, of the fifth or sixth aspects, the proteases determined are active elastase, MMP-1 and MMP-9.

In the aspects and embodiments defined herein above and below, the at least one elastase and at least one endogenous matrix metalloproteinase may be endogenous proteases. Typically, said endogenous proteases are human endogenous proteases.

In another embodiment of the fifth aspect, the invention provides a diagnostic apparatus according to the fifth aspect, wherein the step of determining comprises establishing whether the combined amount of said proteases falls within a predetermined range.

In another embodiment of the fifth aspect, the invention provides a diagnostic apparatus according to the fifth aspect, wherein the step of determining comprises comparing the combined amount of said proteases with a control standard.

In a further embodiment, the step of determining comprises the additional step of providing an output signal indicating the result of the comparison between the combined amount of said proteases and said control standard. Output signals may be of any suitable form as apparent to the skilled person. Suitable signals are disclosed herein. For example, output signals may be visual or auditory, and may be immediately recognisable (e.g. written text) or may require further interpretation by reference to a standard (e.g. a colour signal).

The devices according to the present invention may comprise a first element specifically adapted to measure the level of one or more protease enzymes, and one or more further elements specifically adapted to measure the level of one or more other protease enzymes. In certain embodiments, the apparatus comprises a single element specifically adapted to measure the level of all analyte proteases, either separately or as a weighted average (weighted sum) in combination. For example, a single diagnostic device may be specifically adapted for detecting each of said proteases in said sample. Suitably, the apparatus or devices according to the present invention may contain diagnostic test devices specifically adapted for detecting the proteases. For example, the apparatus may comprise a first device specifically adapted to measure the level of one protease enzyme, and one or more further devices specifically adapted to measure the level of each remaining protease. Suitably, the apparatus comprises a single device specifically adapted to measure the level of all proteases. For example, in one embodiment, the present invention provides a diagnostic apparatus according to any preceding aspect or embodiment, wherein the apparatus comprises a single diagnostic device specifically adapted for detecting each of said proteases in said sample.

The term "specifically adapted" herein signifies that the device comprises at least one substance that reacts selectively with the protease analyte.

The device or substance may comprise a selective binding partner such as an immunological binding partner, for the protease analyte and/or for a substrate peptide for the protease analyte, and/or for a cleavage fragment of said substrate peptide, and/or for a marker moiety attached to said substrate peptide. Suitable immunological binding partners include polyclonal antibodies and monoclonal antibodies. In other embodiments, the substance may comprise a specific substrate for the analyte, for example a peptide sequence that is cleaved selectively by an analyte protease enzyme. Suitably, the selective reagent is immobilized in the device, for example by chemical or physical bonding to a solid substrate in said device, as described in more detail below.

As noted above, a diagnostic apparatus according to the present invention may contain one or more selective binding partners to bind the one or more analyte molecules present in the sample. Suitable immunological binding partners include polyclonal antibodies and monoclonal antibodies as stated above.

If polyclonal antibodies are desired, a selected mammal, such as a mouse, rabbit, goat or horse, may be immunised with the monitored marker. The monitored marker used to immunise the animal can be obtained by any suitable technique, for example, it can be purified from a wound fluid sample from an infected wound, it can be derived by recombinant DNA technology or it can be synthesized chemically. If desired, the monitored marker can be conjugated to a carrier protein. Commonly used carriers to which the monitored markers may be chemically coupled include bovine serum albumin, thyroglobulin and keyhole limpet haemocyanin. The optionally coupled monitored marker is then used to immunise the animal. Serum from the immunised animal is collected and treated according to known procedures, for example by immunoaffinity chromatography. Monoclonal antibodies to the monitored marker can also be readily produced by one skilled in the art. The general methodology for making monoclonal antibodies using hybridoma technology is well known.

Panels of monoclonal antibodies produced against the monitored marker can be screened for various properties, i.e., for isotype, epitope, affinity, etc. Alternatively, genes encoding the monoclonal antibodies of interest may be isolated from hybridomas, for instance by PCR techniques known in the art, and cloned and expressed in appropriate vectors. Chimeric antibodies, in which non-human variable regions are joined or fused to human constant regions may also be of use. Humanised antibodies may also be used. The term "humanised antibody", as used herein, refers to antibody molecules in which the CDR amino acids and selected other amino acids in the variable domains of the heavy and/or light chains of a non-human donor antibody have been substituted in place of the equivalent amino acids in a human antibody. The humanised antibody thus closely resembles a human antibody but has the binding ability of the donor antibody. In a further alternative, the antibody may be a "bispecific" antibody, that is, an antibody having two different antigen binding domains, each domain being directed against a different epitope.

Phage display technology may be utilised to select genes which encode antibodies with binding activities towards the monitored marker either from repertoires of PCR amplified V-genes of lymphocytes from humans screened for possessing the relevant antibodies, or from naive libraries. The affinity of these antibodies can also be improved by chain shuffling.

Where antibodies generated by the above techniques, whether polyclonal or monoclonal, are employed as reagents in immunoassays, radioimmunoassays (RIA) or enzyme-linked immunosorbent assays (ELISA), the antibodies can be labelled with an analytically-detectable reagent such as a radioisotope, a fluorescent molecule or an enzyme.

As used herein, the term "antibody" refers to intact molecules as well as to fragments thereof, such as Fab, F(ab')2 and Fv, which are capable of binding to the antigenic determinant in question. Such antibodies thus bind to the monitored marker.

Suitably, the immunological or other binding partners are immobilised on a solid support material, for example by avidin-biotin linking, or dialdehyde derivatization of the support material, followed by cross-linking to a peptide binding partner. The apparatus (device) may further comprise other immunological binding partners and/or reagents or indicator molecules may for example in a solution that is added to the wound fluid sample.

In some embodiments or aspects of the present invention, the apparatus (device) comprises a solid support material having an immunological binding partner for an analyte moiety covalently linked thereto. The solid support materials bearing immunological or other binding partners may be used in a range of immunoassays to analyse the presence of the analytes of interest. For example, the support having antibodies or antibody fragments bound thereto may be used in sandwich immunoassay-type analysis. Alternatively, the support may have analog ligands bound to the antibodies, whereby the molecules present in the wound fluid are detected by affinity displacement immunoassay. Various other immunoassays will be apparent to persons skilled in the art.

The analytes of interest are protease enzymes that can modify substrates such as proteins or polypeptides, by cleavage. Such modification of peptide substrates can be detected to determine the presence or absence of the analyte in a sample. In embodiments, the present invention provides a diagnostic device (apparatus) according to any preceding aspect or embodiment wherein the apparatus/device comprises an indicator moiety that is immobilized or inhibited by a chemical moiety, wherein the chemical moiety comprises an exogenous peptide substrate for at least one of the analyte protease enzymes, and the exogenous peptide substrate is cleavable by the said at least one analyte protease enzymes to release or activate the indicator moiety.

Suitably, the indicator moiety comprises an indicator enzyme, an enzyme cofactor, a dye, a radioactive moiety, a spin label, a luminescent moiety or a fluorophore. Suitably, the indicator moiety comprises an indicator enzyme or a fluorophore. Suitable indicator enzymes may for example be selected from the group consisting of a laccase (CotA enzyme), alkaline phosphatase, p-galactosidase, acetylcholinesterase, green fluorescent proteins, luciferases and horseradish peroxidases. Suitable fluorophores include umbelliferone, fluorescein, fluorescein isothiocyanate, rhodamine, dichlorotriazinylamine fluorescein, dansyl chloride, coumarin derivatives such as 7-amino-4-methyl coumarin, and phycoerythrin. Suitable luminescent moieties include luminol, luciferase, luciferin, and aequorin.

In the devices in which the indicator moiety comprises an enzyme, the device suitably further comprises a substrate that interacts with the indicator enzyme to give a detectable spectrophotometric, colorimetric, fluorimetric, luminescent, electrochemical or radioactive signal.

In certain embodiments, the indicator moiety comprises an indicator enzyme and the chemical moiety inhibits the indicator enzyme by sterically hindering an active site of the indicator enzyme, or by causing the indicator enzyme to fold into an inactive conformation. Alternatively or additionally, the chemical moiety may tether the enzyme to a solid substrate, whereby release from the substrate by action of the analyte protease activates the enzyme and/or allows the enzyme to migrate to a remote substrate location where it reacts with a suitable substrate (which may be immobilized at the remote location) to give a detectable signal. In yet other embodiments, the device comprises two indicator enzyme moieties linked by the chemical moiety, and cleavage of said peptide by the host-derived protease enzyme results in activation of both enzyme moieties.

In other embodiments, the device comprises an indicator enzyme, and a cofactor for the enzyme that is immobilized or inhibited by the chemical moiety, whereby cleavage of peptide releases or activates the cofactor.

A currently preferred indicator moiety comprises colloidal particles, suitably colloidal gold particles, conjugated to a peptide such as an antibody or a peptide substrate in known fashion. The colloidal particles are coloured, whereby accumulation of the colloidal particles in a test region or a control region of the device gives a visible colour the intensity of which increases with concentration of the particles, thereby allowing quantitative colorimetric determination of said concentration by colorimetry and/or comparison of the observed colour intensity with a reference colour to evaluate if the threshold has been exceeded.

In certain embodiments, the indicator moiety is tethered to a solid substrate by said chemical moiety, and is released from said substrate by cleavage of said exogenous peptide substrate by said protease. In embodiments, the indicator moiety is conjugated to the exogenous peptide substrate, or to an immunological binding partner for the exogenous peptide substrate, and the protease level is determined by sandwich-immunoassay techniques involving binding of the exogenous peptide substrate to immunological binding partner for the exogenous peptide substrate. It will be appreciated that, in these embodiments, either the exogenous peptide substrate or the immunological binding partner for the exogenous peptide substrate may be anchored to a solid substrate.

One method for detecting the modification of a substrate by an enzyme is to label the substrate with two different dyes, where one dye serves to quench the fluorescence of the other dye by fluorescence resonance energy transfer (FRET) when the dye molecules are in close proximity A typical acceptor and donor pair for resonance energy transfer consists of 4-[[-(dimethylamino)phenyl]azo]benzoic acid (DABCYL) and 5-[(2-aminoethylamino]naphthalene sulfonic acid (EDANS). EDANS is excited by illumination with a wavelength of 336 nanometers, and emits a photon with a wavelength of 490 nanometers. If a DABCYL moiety is located within 2 nanometers of the EDANS, this photon will be efficiently absorbed. DABCYL and EDANS can be attached to opposite ends of a peptide in the diagnostic material used in the systems of the present invention. If the peptide is intact, FRET will be very efficient. If the peptide has been cleaved by an enzyme analyte, the two dyes will no longer be in close proximity and FRET will be inefficient. The cleavage reaction can be followed by observing either a decrease in DABCYL fluorescence or an increase in EDANS fluorescence (loss of quenching).

Another suitable diagnostic material for use in the systems of the present invention comprises a chromogenic dye conjugated to a solid support by a suitable cleavable substrate moiety, such as a peptide. The chromogenic dye will change color when the linker group is cleaved by the enzyme of interest. For example, para-nitrophenyl is colorless when linked to the support, and turns yellow when cleaved. The analyte concentration can be determined by measuring absorbance at 415 nanometers. Other dyes that produce detectable color change upon cleavage are known to those skilled in the art.

In yet another embodiment, the diagnostic material may comprise a colored support having a differently-colored molecule conjugated thereto by a linker moiety that can be cleaved by an analyte enzyme in the sample. Cleavage of the dye from the colored support can thereby result in a color change of the diagnostic material.

The solid support materials used for the above identified assays of enzyme activity and immunoassays may comprise any suitable natural or synthetic polymer, including insoluble polysaccharides such as cellulose or nitrocellulose, and synthetic polymers such as polyacrylates. The cleavable cross-linkages, where present, generally comprise cleavable oligopeptidic sequences or cleavable oligosaccharides, each typically of twenty residues or fewer, for example from 3 to 15 residues.

The sensitivity of the diagnostic material will depend on a number of factors, including the length of the cleavable linker sequences. Steric hindrance may also be reduced by coupling the cleavable oligopeptidic sequence to the polymer by means of an appropriate spacer. Thus, the oligopeptidic sequences may couple the polymers directly (in which case the cross-linkage consists of the oligopeptidic sequence) or by means of an appropriate spacer. Suitable conjugation methods incorporating spacers are described in U.S. Pat. No. 5,770,229.

Particularly suitable chemical systems for use in the devices of the present invention are described in WO03/063693 and WO2005/021780, the entire contents of which are incorporated herein by reference.

In one embodiment, the indicator enzyme is a laccase that has been inhibited by the peptide substrate. Laccase (diphenol oxidase) is a member of the multi-copper oxidase family of enzymes. Generally, these enzymes require oxygen to oxidize phenols, polyphenols aromatic amines, and other non-phenolic substrates by one electron to create a radical species. It is a suitable indicator enzyme in part due to its stability and oxidation properties. The oxidation of species results in an upaired electron which generates a color change. CotA is highly thermostable.

CotA can be used in the apparatus and devices of the present invention by modifying the sequence to generate a proenzyme form. Analysis of the structure of CotA indicates that an extension of suitable length appended onto the N-terminus of CotA can allow an appended inhibitor to be placed in the active site of the enzyme. The extension peptide is selected to be a cleavage target of the analyte protease. This will allow the blocking extension to be cleaved in the presence of the analyte protease. Analysis of the x-ray structure of CotA has shown that the length of the amino acid chain needed to reach the shortest distance around the structure is about 3 nm.

The modified enzymes with the peptide extension block can be prepared and screened for suitability using standard recombinant methods as described in more detail in WO2005/021780.

As already noted, the endogenous proteases to be detected include human neutrophil elastase. For elastase, suitable substrate linkers may include one or more of the oligopeptidic sequences Lys-Gly-Ala-Ala-Ala-Lys-Ala-Ala-Ala-Ala- (SEQ ID NO: 1), Ala-Ala-Pro-Val (SEQ ID NO: 2), Ala-Ala-Pro-Leu (SEQ ID NO: 3), Ala-Ala-Pro-Phe (SEQ ID NO: 4), Ala-Ala-Pro-Ala (SEQ ID NO: 5) or Ala-Tyr-Leu-Val (SEQ ID NO: 6). For example, the substrate may be MeOSuc-Ala-Ala-Pro-Val-AMC (SEQ ID NO: 7), wherein MeOsuc is a succinyl methyl ester residue and AMC is a 7-amino-4-methyl coumarin residue.

The proteases to be detected also include matrix metalloproteinases, such as MMP-1 and MMP-9. Suitable cleavable linkers for matrix metalloproteinases may comprise the oligopeptidic sequence -Gly-Pro-Y-Gly-Pro-Z- (SEQ ID NO: 8), -Gly-Pro-Leu-Gly-Pro-Z- (SEQ ID NO: 9), -Gly-Pro-Ile-Gly-Pro-Z- (SEQ ID NO: 10), or -Ala-Pro-Gly-Leu-Z- (SEQ ID NO: 11), where Y and Z are amino acids.

Fragments and sequence variants of the polypeptides and nucleic acids described above may also be used in the apparatus (devices) and methods of the present invention. Functional variants can contain substitution of similar amino acids that result in no change or an insignificant change in function. Alternatively, such substitutions may positively or negatively affect function to some degree.

In certain embodiments, the apparatus or device(s) according to the present invention comprise, or consist essentially of a wound dressing, dipstick or swab. In one embodiment, the invention provides a diagnostic apparatus according to any preceding aspect or embodiment, comprising a dip-stick or swab for sampling of said wound fluid.

Immobilisation of reaction components onto a dipstick, wound mapping sheet or other solid or gel substrate offers the opportunity of performing a more quantitative measurement. For example, in the case of a reaction linked to the generation of a colour the device may be transferred to a spectrometer. Suitable methods of analysis will be apparent to those of skill in the art.

Immobilisation of the reaction components to a small biosensor device will also have the advantage that less of the components (such as enzyme and substrate) are needed. The device will thus be less expensive to manufacture than a dressing that needs to have a large surface area in order to allow the mapping of a large wound area.

Methods for the incorporation of the components of the assay reaction onto a clinical dressing, "dipstick", sheet or other biosensor are routine in the art. See for example Fagerstam and Karlsson (1994) *Immunochemistry,* 949-970.

In one embodiment, the method, apparatus or device of the invention comprises a reference assay element for determining the total protein content of the sample, so that the measured levels of marker can be normalised to constant total protein level in order to increase accuracy.

In certain embodiments, the apparatus or device according to the present invention comprises a housing containing one or more reagents and having an inlet provided therein for introduction of the sample. The housing may be at least partially transparent, or may have windows provided therein, for observation of an indicator region that undergoes a color or fluorescence change. In embodiments, the housing is in the form of a folding card. Suitably the folding card has two flaps joined by a hinge. A diagnostic strip is attached to the first flap. The second flap can fold over the first flap, and suitably a securing feature such as a retaining flap or adhesive strip is provided to secure the card in the folded-over configuration. A window is suitably provided in the first flap for observation of an indicator region of the test strip when second flap is folded over the first flap. A swab carrying a sample of wound fluid can be folded inside the card with the swab abutting an inlet region of the test strip. An opening may be provided in the first flap above said inlet region of the test strip when the card is closed, so that one or more drops of elution fluid can be applied to the swab enclosed inside the folded card.

In certain embodiments, the device operates on the lateral flow principle. That is to say, said device comprises a housing having an inlet for the sample and side walls or a liquid-permeable strip defining a fluid lateral flow path extending from the inlet. By "lateral flow", it is meant liquid flow in which the dissolved or dispersed components of the sample are carried, suitably at substantially equal rates, and with relatively unimpaired flow, laterally through the carrier. Suitably, the fluid flow path contains one or more porous carrier materials. The porous carrier materials are suitably in fluid communication along substantially the whole fluid flow path so as to assist transfer of fluid along the path by capillary action. Suitably, the porous carrier materials are hydrophilic, but suitably they do not themselves absorb water. The porous carrier materials may function as solid substrates for attachment of reagents or indicator moieties. In certain embodiments of the present invention, the device further comprises a control moiety located in a control zone in said device, wherein the control moiety can interact with a component of the wound fluid sample to improve the accuracy of the device.

The size and shape of the carrier are not critical and may vary. The carrier defines a lateral flow path. Suitably, the porous carrier is in the form of one or more elongate strips or columns. In certain embodiments, the porous carrier is one or more elongate strips of sheet material, or a plurality of sheets making up in combination an elongate strip. One or more reaction zones and detection zones would then normally be spaced apart along the long axis of the strip. However, in some embodiments the porous carrier could, for example be in other sheet forms, such as a disk. In these cases the reaction zones and detection zones would normally be arranged concentrically around the center of the sheet, with a sample application zone in the center of the sheet. In yet other embodiments, the carrier is formed of carrier beads, for example beads made from any of the materials described above. The beads may suitably be sized from about 1 micrometer to about 1 mm. The beads may be packed into the flow path inside the housing, or may be captured or supported on a suitable porous substrate such as a glass fiber pad.

As discussed above, the apparatus or device(s) according to the present invention are adapted to detect more than one analyte or protease. In one embodiment, a single device may be adapted to detect each of the proteases to be determined. For example, a single device may be adapted to detect each of the elastase and matrix metalloproteinases to be determined such as active elastase, MMP-1 and MMP-9, e.g. neutrophil elastase, MMP-1 and MMP-9. Alternatively, a single device may be adapted to detect the protease enzymes and their respective protease enzyme inhibitors, Suitably, a single device may be adapted to detect the protease enzymes but not their respective protease enzyme inhibitors. In any of these cases, the detection of more than one protease or other analyte can be done by the use of several different reagents in a single reaction zone, or suitably by the provision in a single device of a plurality of lateral flow paths each adapted for detecting a different analyte. In certain embodiments, the plurality of lateral flow paths are defined as separate fluid flow paths in the housing, for example the plurality of lateral flow paths may be radially distributed around a sample receiving port. In some embodiments, the plurality of fluid flow paths are physically separated in a housing. In other embodiments multiple lateral flow paths (lanes) can be defined in a single lateral flow membrane by depositing lines of wax or similar hydrophobic material between the lanes. In yet other embodiments, the substrate is reactive with more than one, or all, of the protease analyte enzymes to different degrees, whereby a single measurement gives a weighted average, also defined as an average protease activity weighted by said respective reactivities.

The apparatus or device(s) of the apparatus according to the present invention may for example be incorporated into a bacterial sensing device of the kind described in UK patent application GB-A-2422664 filed on 28 Jan. 2005, the entire content of which is incorporated herein by reference.

An absorbent element may suitably be included in these devices of the present invention. The absorbent element is a means for drawing the whole sample through the device by capillary attraction. The absorbent element is thus usually located at a downstream end of the flow path. Generally, the absorbent element will consist of a hydrophilic absorbent material such as a woven or nonwoven textile material, a filter paper or a glass fiber filter.

The apparatus or device(s) according to the present invention may further comprise at least one filtration element to remove impurities from the sample before the sample undergoes analysis. The filtration device may for example comprise a microporous filtration sheet for removal of cells and other particulate debris from the sample. The filtration device is typically provided upstream of the sample application zone of the fluid flow path, for example in the inlet of the housing or in the housing upstream of the inlet.

In certain embodiments, the apparatus or devices according to the present invention include a control moiety in a control zone of the device, wherein the control moiety can interact with a component of the wound fluid sample to improve the accuracy of the device. Suitably, the control zone is adapted to reduce false positive or false negative results. A false negative result could arise for various reasons, including (1) the sample is too dilute, or (2) the sample was too small to start with.

In order to address false negative mechanism, the control zone suitably further comprises a reference assay element for determining the total protease content or the total protein content of the sample, that is to say for establishing that the total protease content or the total protein content of the sample is higher than a predetermined minimum. It is possible to indicate the presence of protein by the use of tetrabromophenol blue, which changes from colorless to blue depending on the concentration of protein present. It is also possible to detect glucose (using glucose oxidase), blood (using diisopropyl-benzene dihydroperoxide and tetramethylbenzidine), leukocytes (using ester and diazonium salt). These may all be useful analytes for detection in the control zone for the reduction of false negatives.

Lateral flow devices that may be used with suitable modification are described, for example, in WO-A-2009024805, WO-A-2007128980, WO-A-2009063208 and WO-A-2006079826, the entire disclosures of which are incorporated herein by reference. The devices described in WO-A-2007128980 are especially suitable. These devices produce an output in the form of a colored line in an indicator region of the lateral flow substrate. The colour intensity of this line can be compared with a reference chart, or measured with a colorimeter, to determine if the threshold has been exceeded. It will be appreciated that other indicators could give a detectable fluorescence which can be compared with reference values to determine if the threshold has been exceeded.

Suitably, these devices are lateral flow devices wherein the sample is initially reacted with a protease analyte substrate (such as an exogenous peptide substrate) conjugated to a binding moiety, such as an immunological binding moiety or biotin. The sample is also mixed with a chromophore (such as colloidal gold) conjugated to a binding partner (such as an antibody) specific for the protease analyte substrate. In the absence of protease, the chromophore-binding partner conjugate binds to the substrate-binding moiety conjugate to form a complex containing both the binding moiety and the chromophore. In the presence of protease, the substrate is cleaved whereby little or no binding of the above components takes place. The mixture is introduced into a lateral flow strip having a sample line for selectively binding the binding moiety and a control line for selectively binding the binding partner. In the absence of protease, the above complex is bound at the sample line resulting in colour at the sample line. In the presence of protease, less of the above complex is formed and therefore less colour is observed at the sample line. In both cases, chromophore-binding partner (present in excess in the starting mixture) is bound at the control line to give a colour indicative of a completed test.

In certain embodiments, the apparatus according to the present invention may further comprise one or more components selected from a color chart for interpreting the output of the diagnostic device, a sampling device for collecting a sample of a biological fluid such as a wound fluid; a wash liquid for carrying a sample of fluid through the device, and a pretreatment solution containing a reagent for pretreatment of the fluid sample. In a further aspect, the present invention provides a diagnostic kit comprising a diagnostic device according to any preceding aspect or embodiment, together with one or more of: a color chart for interpreting the output of the diagnostic device, a sampling device for collecting a sample of a biological fluid such as a wound fluid; a wash liquid for carrying a sample of fluid through the device, and a pretreatment solution containing a reagent for pretreatment of the fluid sample.

Where present, the sampling device may comprise a swab or a biopsy punch, for example a shaft having a swab or biopsy punch attached thereto. The swab may be any absorbent swab, for example a nonwoven fibrous swab. Typically the diameter of the swab is about 2 to about 5 mm, for example about 3 mm. In certain embodiments, the swab may be formed from a medically acceptable open-celled foam, for example a polyurethane foam, since such foams have high absorbency and can readily be squeezed to expel absorbed fluids. The biopsy punch will typically be a stainless steel cylindrical punch of diameter about 1 mm to about 10 mm, for example about 3 mm to about 8 mm, suitably about 6 mm.

Suitably, in embodiments of the present invention, the diagnostic device includes a sample receiving port, and suitably the sample receiving port and the swab or biopsy punch comprise complementary fitting elements whereby the swab or biopsy punch can be secured to the device with the swab or biopsy punch received in the sample receiving port.

In certain embodiments the fitting element on the shaft may be located from 1 mm to about 30 mm from the base of the swab or the biopsy punch. This is consistent with the use of relatively small sample receiving port on the housing of the diagnostic device. The sample receiving port is typically located on an upper surface of the diagnostic device, and it is typically generally in the form of an upwardly projecting tube, open at the top and having the inlet to the fluid flow path located at the bottom of the tube. Suitable swabs, biopsy punches and sample receiving caps are described in detail in UK patent applications GB-A-2411230 and GB-A-2411231 both filed on 23 Feb. 2004, the entire contents of which are incorporated herein by reference.

The fitting element on the shaft may a tapered region of the shaft for forming an interference fit with the housing, for example it may appear as a truncated cone that is coaxial with the shaft and tapers towards the first end of the shaft. Or the whole shaft may have a diameter larger than that of the swab or biopsy punch, with a tapered region adjacent to the first end. In any case, the diameter of the tapered region where it engages with the housing is normally greater than the diameter of the swab or biopsy punch, so that the inlet port can enclose the swab or biopsy punch.

In other embodiments, the engagement element may comprise a snap-fitting projection for forming a snap-fit with one or more complementary projections on an inner surface of the housing, or a threaded projection for forming a screw fit with one or more complementary threads on an inner surface of the cap, or a Luer-lock type fitting.

In certain embodiments the shaft is hollow, whereby a fluid can be passed down the shaft from the second end to expel the biological sample from the swab or the biopsy punch into the diagnostic device. This helps to ensure that the entire sample passes through the device, thereby avoiding false negatives. The shaft may comprise a fitting at the second end for attachment of a syringe or other source of the fluid. In certain embodiments, the apparatus may comprise a reservoir of liquid attached to the second end of the shaft, for example a compressible bulb containing the liquid, which can be activated after use of the swab or biopsy punch. Suitable devices of this kind are described, for example in U.S. Pat. No. 5,266,266, the entire content of which is incorporated herein by reference. In other embodiments, the apparatus may comprise a plunger that can be pushed down the hollow bore of the shaft to expel fluid or other specimens from the swab or biopsy punch.

Another advantage of the hollow shaft is that, where the apparatus is a biopsy punch, the biopsy sample can more readily be pushed or blown out of the punch. The biopsy punch apparatus can further comprise a homogenizing tool that can be passed down the hollow shaft to homogenize a tissue sample in the biopsy punch. This step of homogenizing can be followed, if necessary, by passing liquid down the shaft from the second end to expel the homogenized tissue from the biopsy punch into the device for diagnostic analysis.

The swab or biopsy punch may be sterilized, and may be packaged in a microorganism-impermeable container.

In a seventh aspect, the present invention provides a kit comprising a diagnostic apparatus according to the fifth or sixth aspects or embodiments of these aspects as described above and a wound dressing.

In a eighth aspect, the present invention provides a method for predicting whether a subject would be responsive to treatment of a wound that exudes a wound fluid, the method comprising simultaneously or sequentially determining the amount of at least one elastase and at least one matrix metalloproteinase in the wound fluid wherein the amounts of protease inhibitors in the wound sample are not determined.

In a ninth aspect, the present invention provides a method for predicting whether a subject would be responsive to treatment of a wound that exudes a wound fluid, the method comprising simultaneously or sequentially determining the amount of elastase, MMP-1 and MMP-9 in the wound fluid.

In one embodiment of the eighth or ninth aspect, the treatment comprises applying a wound dressing to the wound.

In a tenth aspect, the invention provides a method for treating a wound that exudes a wound fluid, comprising the steps of:
(a) simultaneously or sequentially determining the amount of at least one elastase and at least one matrix metalloproteinase in the wound fluid wherein the amounts of protease inhibitors in the wound sample are not determined; and
(b) applying a wound dressing to the wound.

In a eleventh aspect, the invention provides a method for treating a wound that exudes a wound fluid, comprising the steps of:
(a) simultaneously or sequentially determining the amount of elastase, MMP-1 and MMP-9 in the wound fluid; and
(b) applying a wound dressing to the wound.

In an twelfth aspect, the invention provides a method for treating a wound that exudes a wound fluid, comprising the steps of:
(a) simultaneously or sequentially determining the amount of at least one elastase and at least one matrix metalloproteinase in the wound fluid at a point in time, wherein the amounts of protease inhibitors in the wound sample are not determined;
(b) applying a wound dressing to the wound;
(c) simultaneously or sequentially determining the amount of at least one elastase and at least one matrix metalloproteinase in the wound fluid at a subsequent point in time, wherein the amounts of protease inhibitors in the wound sample are not determined; and
(d) applying a wound dressing to the wound if the combined amount of the at least one elastase and at least one matrix metalloproteinase in the wound fluid in step (c) is indicative of a wound that would respond well to wound treatment.

In a thirteenth aspect, the invention provides a method for treating a wound that exudes a wound fluid, comprising the steps of:
(a) simultaneously or sequentially determining the amount of elastase, MMP-1 and MMP-9 in the wound fluid at a point in time;
(b) applying a wound dressing to the wound;
(c) simultaneously or sequentially determining the amount of elastase, MMP-1 and MMP-9 in the wound fluid at a subsequent point in time; and
(d) applying a wound dressing to the wound if the combined amount of the elastase, MMP-1 and MMP-9 in the wound fluid in step (c) is indicative of a wound that would respond well to wound treatment.

Typically, in the ninth, eleventh or thirteenth aspects, the amounts of protease inhibitors in the wound sample are not determined.

In some embodiments of the above fifth to thirteenth aspects or embodiments of these aspects, the step of determining comprises establishing whether the combined amount of the proteases falls within a predetermined range; and/or comparing the combined amount of said proteases with a control standard.

In some embodiments of the above fifth to thirteenth aspects, the step of applying a wound dressing to the wound is performed only when the amount of the protease is determined to fall within a predetermined range that is indicative of a wound that would respond well to wound treatment as described above; or if a comparison of the combined amount of proteases with a control indicates that the wound would be responsive to treatment with said wound dressing. This provides the benefit of minimising the treatment of patients that would be likely to be unresponsive to said treatment.

Suitably, the wound dressings defined above in relation to any of the seventh to thirteenth aspects of the invention are as hereinbefore defined in relation to the fifth or sixth aspects of the invention. Suitably, the step of determining the amount of proteases in relation to any of the seventh to thirteenth aspects of the invention is performed by means of an apparatus or device according to the fifth or sixth aspects or of any embodiment of the fifth or sixth aspects disclosed above by one of the methods hereinbefore described in relation to the fifth or sixth aspects of the invention.

In suitable aspects or embodiments of the above aspects, the wound being assayed, monitored, sampled or treated has not previously been dressed by a wound dressing. In typical embodiments of the above aspects, the wound being assayed, monitored, sampled or treated has not previously been dressed by a wound dressing comprising oxidised cellulose, such as a wound dressing comprising collagen/ORC.

Suitably, the wound dressing according to aspects of the present invention includes a wound contacting material comprising the oxidized cellulose. The term "wound contacting material" encompasses materials that do not contact the wound surface directly, but that contact the wound fluid e.g. through a porous top sheet. The wound contacting material is normally the wound contacting layer of the dressing in use, and may for example be selected from the group consisting of woven, nonwoven and knitted fabrics, freeze-dried sponges and solvent-dried sponges comprising the oxidized cellulose. The wound contacting material may comprise at least 10% of oxidized cellulose, for example at least 20% or at least 30% by weight of oxidized cellulose.

The methods according to the above aspects of the present invention may comprise an aqueous assay step. Wound fluid may be extracted directly from the environment of the wound, or can be washed off the wound using a saline buffer. The resulting solution can then be assayed for the concentration of the marker in, for example, a test tube or in a microassay plate.

Such a method will be preferable for use in cases in which the wound is too small or too inaccessible to allow access of a diagnostic device such as a dipstick. This method has the additional advantage that the wound exudate sample may be diluted. The values obtained for a diluted sample of wound fluid may be normalised relative to the total protein concentration in the sample. Total protein concentration can be calculated as described in Example 4.

It will be clear that an aqueous assay system is more applicable to use in a laboratory environment, whereas a diagnostic device containing the necessary reaction components will be more suitable for use in a hospital or domestic environment.

Treatment of Conditions

The apparatus, devices, kits and methods of the present invention are useful in prognosing or treating wounds particularly wounds that exude a wound fluid. Any type of wound may be diagnosed for treatment using the apparatus and methods of the present invention particularly if said wound exudes a wound fluid. For example, the wound may be a chronic or acute wound. The wound is suitably a chronic wound. Suitably, the chronic wound is selected from the group consisting of venous ulcers, pressure sores, decubitis ulcers, diabetic ulcers and chronic ulcers of unknown aetiology. In one embodiment the wound is an acute wound. An example of an acute wound is an acute traumatic laceration, perhaps resulting from an intentional operative incision.

To allow measurement of concentration of a protease in the wound fluid, a sample of wound fluid must be added to the measurement apparatus. Measurement may either be made in situ, or fluid may be removed from the wound for analysis in the apparatus or device of the invention. Suitably, the fluid is removed from the wound for analysis.

General

In certain aspects or embodiments thereof according to the present invention, the term "determining" includes measuring a numerical value of said proteases; establishing if the amount or combined amount falls above or below a predetermined range; and/or comparing the numerical value with a control standard. For example, determining includes measuring the activity and or concentration of one or more analytes in a wound sample. Suitably in further aspects or embodiments thereof according to the present invention the term "determining" comprises; measuring the level of elastase and establishing if said level exceeds a first predetermined threshold; and measuring the level of at least one matrix metalloproteinase and establishing if said level exceeds a second predetermined threshold. Suitably, in other aspects or embodiments thereof according to the present invention, the term "determining" comprises establishing whether a weighted average (weighted sum) level of said proteases exceeds a predetermined threshold value for said weighted average.

The term "amount" is used herein to signify the numerical value of a particular analyte (e.g. a protease) in a wound fluid. Typically, the amount of an individual analyte is expressed in terms of its free concentration or its activity. Most typically, the term amount is used to indicate the activity of a particular analyte.

When used herein, the term "combined amount" refers to a single numerical value that results from the application of a mathematical function to a plurality of values, for example those amounts obtained for a number of individual analytes. For example, the term "combined amount" may refer to the sum or product of a group of individual values. Typically, the term "combined amount" relates to the sum of a group of individual values. For example, in suitable embodiments, the amount of elastase refers to elastase-like activity (e.g. in RFU/min/mL) and the amount of metalloproteinase (MMP) refers to total concentration of the respective analyte (e.g. in ng/mL).

When used herein, the term "quantifying" refers to measuring an absolute numerical quantity of a particular analyte(s) or substrate(s) in a sample, within the margins of experimental error.

The term "marker" or "analyte" refers to any chemical entity that is identified or determined using the apparatus, devices, kits or methods defined herein. The markers or analytes determined or identified by the apparatus, devices, kits or methods of the present invention are protease enzymes.

The term "a wound fluid" refers to any wound exudate or other fluid (suitably substantially not including blood) that is present at the surface of the wound, or that is removed from the wound surface by aspiration, absorption or washing. The determining, measuring or quantifying is suitably carried out on wound fluid that has been removed from the body of the patient, but can also be performed on wound fluid in situ. The term "wound fluid" does not normally refer to blood or tissue plasma remote from the wound site. The wound fluid is mammalian wound fluid, suitably human wound fluid.

When used herein, the term "predetermined range" refers to a data range or profile that the skilled person would understand is indicative of a particular sub-class of patient. For instance, the predetermined range may be a data range or profile that is typical of a wound that would respond well to a particular wound treatment, such as oxidised cellulose therapy. Alternatively, the predetermined range may suitably refer to a data range that is typical of a wound that would not respond well to a particular wound treatment, such as oxidised cellulose therapy.

When used herein, the term "predetermined threshold" refers to a minimum level that the skilled person would determine is indicative of a non-healing wound based on statistical analysis of levels determined for known healing and non-healing wounds, for example as explained further below. For the test to be clinically useful, the threshold should be set at an appropriate level so that non-healing wounds with high protease activity are correctly identified. Increasing the threshold will increase the chance of only non-healing wounds being over the threshold. However, if the threshold is too high, wounds that are non-healing due to a high level of proteases would not be identified and clinically this would mean they would not receive the required protease modulating treatment.

When used herein, the term "control standard" or "control" refers to a data set or profile that can be used as a reference or comparison in order to define or normalise another data point or set of data. For instance, the term "control" or "control standard" may be data set or profile that is indicative of a particular sub-class of patient. In Suitably, the control standard may be a data set or profile indicative of healing or non-healing wound status.

Suitably, in other aspects or embodiments of the present invention, the "control" or "control standard" can be a data set or profile that can be used as a comparative tool to allow a skilled person to determine whether a wound is likely to be responsive or non-responsive to a wound treatment, such as oxidised cellulose. In one embodiment, the control standard is a data set or profile indicative of a patient that does not respond well to wound treatment. Typically, the control standard is a data set or profile indicative of a patient that responds well to wound treatment. Patients that tend to respond well to wound treatment as disclosed herein exhibit lower combined amounts of elastase and MMP than patients that tend not to respond well to the treatment. For example, patients that tend to respond well to wound treatment as disclosed herein exhibit lower combined amounts of elastase, matrix metalloproteinase MMP-1 and matrix metalloproteinase MMP-9 in a sample of wound fluid than patients that tend not to respond well to the treatment.

The skilled person would be able to easily identify whether wounds are "responsive to treatment" or not. In particular, the skilled person will readily be able to determine the levels of the proteases identified in the present claims that are predictive or indicative of a good response or poor response to wound treatment, particularly to treatment with wound dressings comprising oxidized cellulose. The terms "responsive" and "responder(s)" as used herein refer to wounds that are considered to respond well to wound treatment, particularly to treatment with oxidized cellulose.

Similarly, "non-responsive" and "non-responder(s)" refers to wounds that are not considered to respond well to wound treatment, particularly to treatment with oxidized cellulose. For instance, patients who exhibit better than 50% wound closure after 4 weeks of wound treatment are considered to be responsive to said treatment.

When used herein, the term "simultaneously" when referring to determining or measuring a plurality markers and/or analytes refers to determining or measuring them substantially at the same time using a single apparatus or device. Alternatively, said determining or measuring simultaneously may be performed using a plurality of apparatus or devices.

When used herein, the term "sequentially" when referring to determining or measuring plurality markers and/or analytes refers to determining or measuring them substantially in succession using a single apparatus or device. Alternatively, said determining or measuring sequentially may be performed using a plurality of apparatus or devices.

When used herein, the term "PROMOGRAN™" refers to the wound dressing commercially available from Systagenix Wound Management, which can be prepared substantially as described in EP-A-1153622.

When used herein, the term "PROMOGRAN PRISMA™" refers to the wound dressing commercially available from Systagenix Wound Management, which can be prepared substantially as described in EP-A-1536845.

The term "comprising" encompasses "including" as well as "consisting of" e.g. an apparatus "comprising" X may consist exclusively of X or may include something additional e.g. X+Y.

The word "substantially" does not exclude "completely" e.g. a composition which is "substantially free" from Y may be completely free from Y. Where necessary, the word "substantially" may be omitted from the definition of the invention.

The term "about" in relation to a numerical value x is optional and means, for example, x+10%.

Aspects of the present invention enable a care giver or a patient to determine quickly and reliably whether a wound is likely to be non-healing, and to select an appropriate therapy based on this determination. For example, non-healing wounds may require the application of special wound dressings such as wound dressings comprising oxidized cellulose, to promote healing.

Accordingly, in a further aspect, the present invention provides a method of treatment comprising determining whether a wound is healing or non-healing in accordance with earlier aspects of the invention, followed by applying an oxidized cellulose containing wound dressing to the wound if it is non-healing or a different kind of dressing if it is healing.

The term "oxidized cellulose" refers to any material produced by the oxidation of cellulose. In suitable embodiments of the invention, the wound dressing provided in aspects of the invention comprises oxidized cellulose. In one embodiment, the oxidized cellulose dressing comprises oxidized regenerated cellulose. Typically, the wound dressing further comprises collagen or chitosan.

For example, oxidation may be performed with dinitrogen tetroxide. Such oxidation converts primary alcohol groups on the saccharide residues to carboxylic acid groups, forming uronic acid residues within the cellulose chain. The oxidation generally does not proceed with complete selectivity, and as a result hydroxyl groups on carbons 2 and 3 are occasionally converted to the keto form. These keto units introduce an alkali labile link, which at pH 7 or higher initiates the decomposition of the polymer via formation of a lactone and sugar ring cleavage. As a result, oxidized cellulose is biodegradable and bioabsorbable under physiological conditions.

A particularly suitable oxidized cellulose for practical applications is oxidized regenerated cellulose (ORC) prepared by oxidation of a regenerated cellulose, such as rayon. It has been known for some time that ORC has haemostatic properties. ORC has been available as a haemostatic product called SURGICEL (Registered Trade Mark of Johnson & Johnson Medical, Inc.) since 1950. This product is produced by the oxidation of a knitted rayon material. A modification of porosity, density and knit pattern led to the launch of a second ORC fabric product, INTERCEED (Registered Trade Mark of Johnson & Johnson Medical, Inc.), which was shown to reduce the extent of post-surgical adhesions in abdominal surgery.

In particular embodiments, the oxidized cellulose in the wound dressing material is complexed with collagen and/or chitosan to form structures of the kind described in WO 98/00180, EP-A-1153622, WO 2004/026200, EP-A-1539258, WO 2004/024197 and/or EP-A-1536845, the entire contents of which are expressly incorporated herein by reference. For example, the oxidized cellulose may be in the form of milled ORC fibres that are dispersed in a freeze-dried collagen or chitosan sponge. This provides for sustained release of the oxidized cellulose to the wound, together with certain therapeutic and synergistic effects arising from the complexation with collagen. Suitably, the weight ratio of oxidized cellulose to collagen and/or chitosan in the wound contacting material is from about 10:1 to about 1:10, for example from about 70:30 to about 30:70. Suitably, the wound contacting material comprises at least 75% on a dry weight basis of oxidized cellulose, collagen and chitosan, more suitably at least 90% and most suitably it consists essentially of oxidized cellulose, collagen and/or chitosan. Such oxidised cellulose wound dressings may also comprise silver. Suitable commercially available wound dressings comprising oxidized cellulose are PROMOGRAN™ and PROMOGRAN PRISMA™ (Systagenix Wound Management).

DESCRIPTION OF THE FIGURES

Embodiments of the invention will now be described further, with reference to the accompanying drawings, in which:

FIG. 8 shows a folding card device according to the present invention with the card in the open configuration;

FIG. 9 shows a detail of the sample receiving well in the device of FIG. 8;

FIG. 10 shows a front view of the folding card device of FIG. 8 in the closed position;

FIG. 11 shows a schematic view of the test reagents present in the sample receiving well of FIG. 9;

FIG. 12 shows a schematic view of the lateral flow test strip in the device of FIG. 8;

FIGS. 13(a) and 13(b) show a schematic of the interaction between the sample, the test strip, and the test reagents for a sample containing low levels of protease analyte;

FIGS. 14(a) and 14(b) show a schematic of the interaction between the sample, the test strip, and the test reagents for a sample containing high levels of protease analyte;

FIG. 15 shows a schematic plan and side view of the lateral flow test strip of the device of FIG. 8.

FIG. 21 provides a box plot analysis of the sum of the concentrations of MMP-1 and MMP-9 in samples of wound fluids taken from patients before the wound treatment program as described in Example 4. The data show no significant difference between the total protein concentration in responders compared to non-responders before treatment.

FIG. 22 provides a box plot analysis of the tumor necrosis factor receptor II (TNFR-II) concentration in samples of wound fluids taken from patients before the wound treatment program as described in Example 4. The data show no significant difference between the total protein concentrations in responders compared to non-responders before treatment.

FIG. 23 provides a box plot analysis of the vascular endothelial growth factor (VEGF) concentration in samples of wound fluids taken from patients before the wound treatment program as described in Example 4. The data show no significant difference between the total protein concentrations in responders compared to non-responders before treatment.

GENERAL METHODS

Methods according to a number of aspects and embodiments of the present invention and suitably relating to determining the healing status of a wound (i.e. whether healing or non-healing) will now be described further with reference to the accompanying drawings, which are described above Clinical Study and Patient Selection All patients enrolled in this study had chronic wounds of at least 30 days duration and a surface area of at least 1 cm$^2$. Exclusion criteria included concomitant conditions or treatments that may have interfered with wound healing and a history of non-compliance that would make it unlikely that a patient would complete the study.

Patients meeting the patient selection criteria were enrolled, and wound fluid collected. Informed consent was obtained from all patients or their authorised representatives prior to study enrolment and the protocol was approved by the Ethics Committee at the participating study centre prior to the commencement of the study. The studies herein were conducted in accordance with both the Declaration of Helsinki and Good Clinical Practice.

Determination of Healing Status

Wherever possible, the wound size was measured and recorded on the day that the swab was taken. The clinicians retrospectively recorded the wound size at Week 2 (2 weeks prior to the swab being taken) and Week 4 (4 weeks prior to the swab being taken) using the patient records. In some cases either Week 4 and/or Week 2 was not available, due to various reasons such as the patient being new to the clinic. The criteria used to classify wounds as healing or non-healing for each ulcer type is described below.

Diabetic foot ulcers were classed as healing if they reached at least 50% reduction by Week 4. Patients that did not meet this criterion by 4 weeks were classed as non-healing. If Week 4 was not available then the wound size at Week 2 was utilised to classify the healing status; if the wound size had increased the patient was classed as non-healing, if the wound had met the 50% reduction within the 2 week timeframe then it was classed as healing, if the wounds had decreased but not met the 50% threshold by 2 weeks this was classed as unknown healing status.

The venous leg ulcers and pressure ulcers were classed as healing if they reached at least 30% reduction by Week 4. Patients that did not meet this criterion by 4 weeks were classed as non-healing. If Week 4 was not available then the wound size at Week 2 was utilised to classify the healing status; if the wound size had increased the patient was designated as non-healing, if the wound had met the 30% reduction in 2 weeks then this was classed as healing, if the wounds had decreased but not met the 30% threshold by 2 weeks this was classed as unknown healing status.

Figure 1:
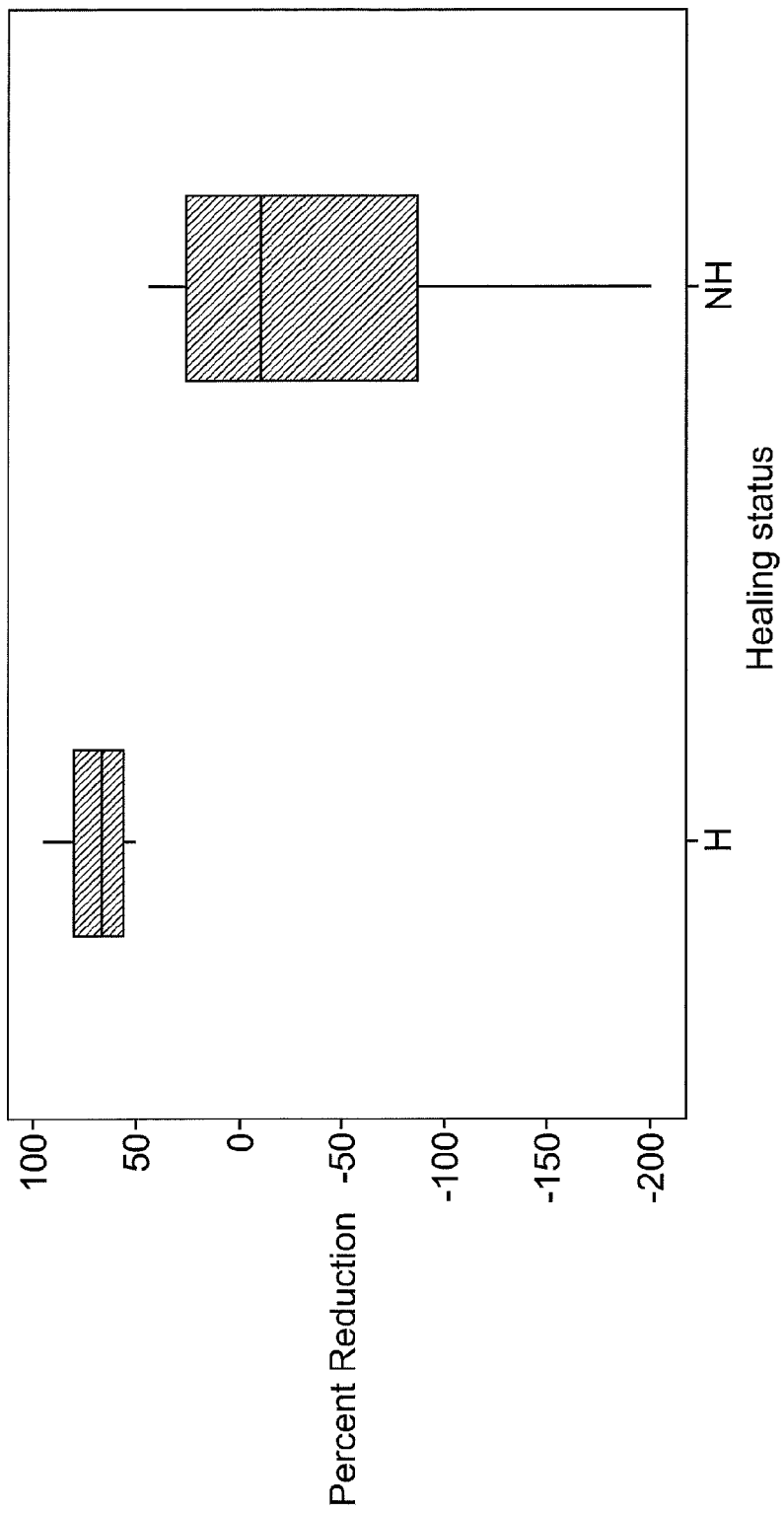
FIG. 1 shows a box plot of measured percentage reduction in wound area after 2 or 4 weeks for healing versus non-healing diabetic foot ulcers.
Figure 2:
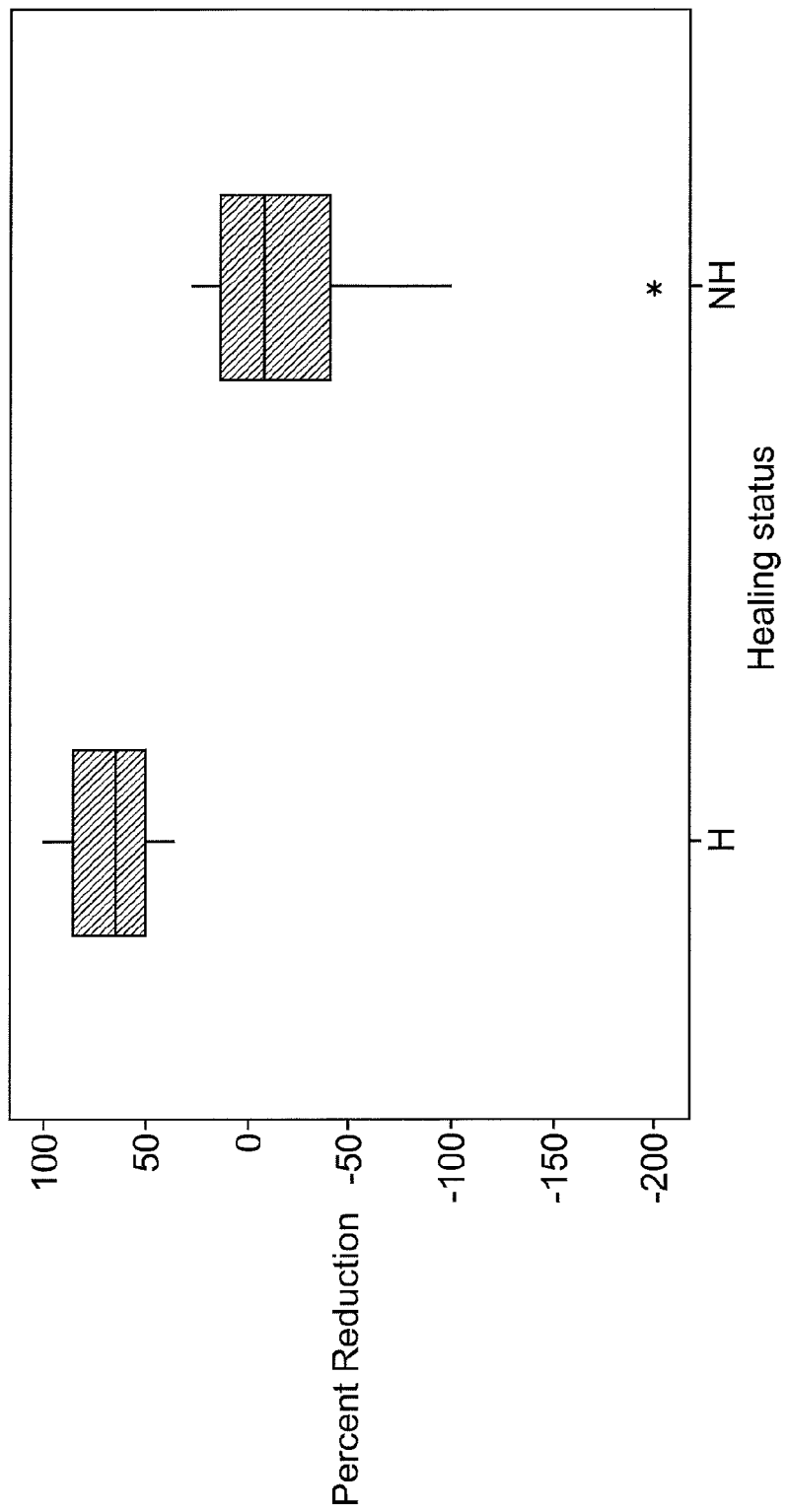
FIG. 2 shows a box plot of measured percentage reduction in wound area after 2 or 4 weeks for healing versus non-healing leg ulcers.
Figure 3:
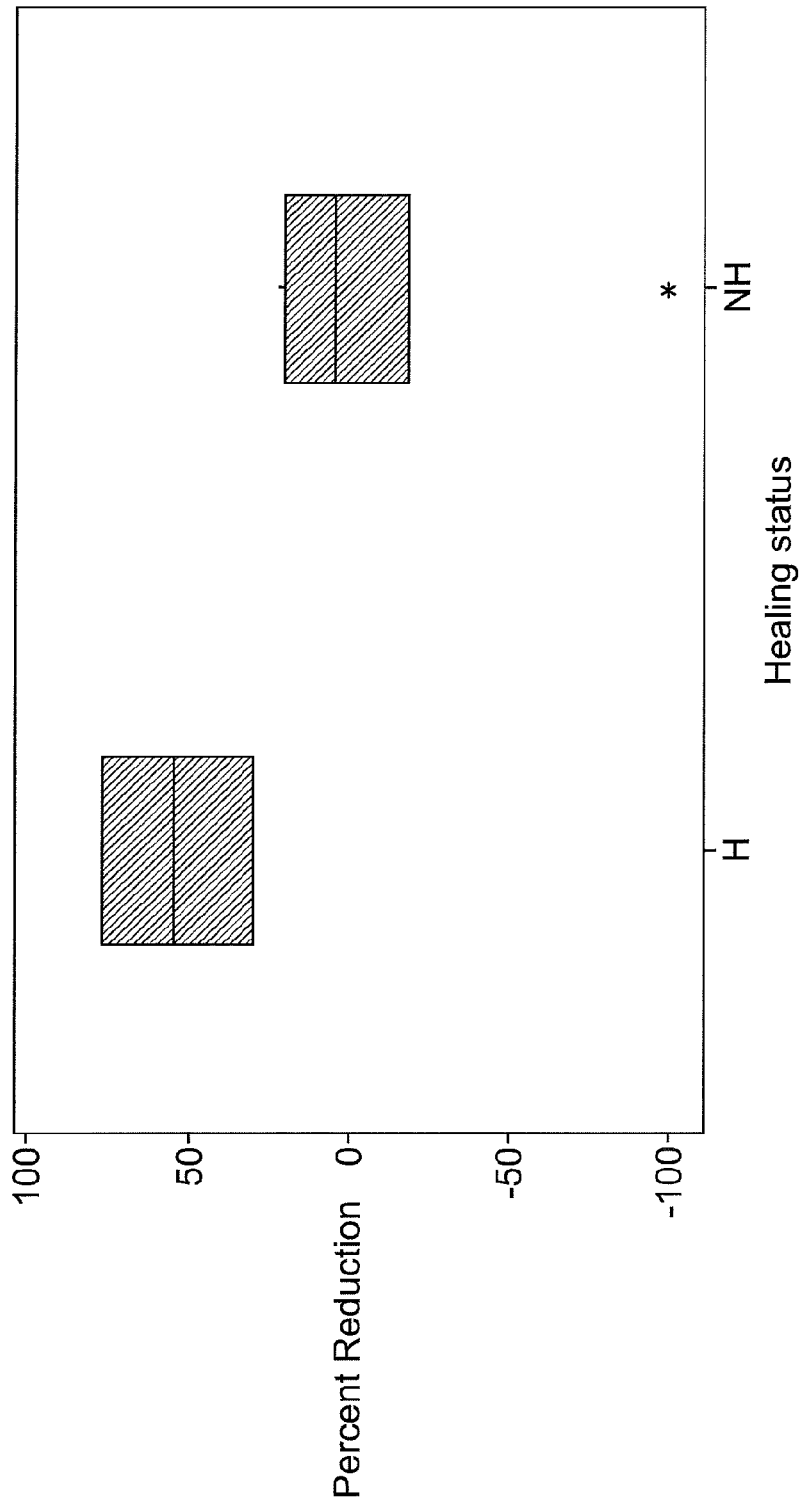
FIG. 3 shows a box plot of measured percentage reduction in wound area after 2 or 4 weeks for healing versus non-healing pressure ulcers.

A summary of the healing data for each wound type is shown in Tables 1-3 below, and graphically in FIGS. 1-3. Results are displayed as percentage decrease in wound size from either Week 4 or Week 2. The data is displayed for each wound type to show the distribution of patients in each group. The maximum increase that has been recorded in this data is an increase in wound size of 200%; therefore any values over this will be classed as a 200% increase. This is so that the data can be clearly viewed on the graphs and the data is not skewed by a few very high values.

TABLE 1

Healing and non-healing diabetic foot ulcers.

|  | Healing (n = 13) | Non-healing (n = 18) |
|---|---|---|
| Range | 51 to 95 (wound size decrease 51 to 95%) | −200 to 45 (200% increase to 45% decrease in wound size) |
| Median % reduction | 67 (67% decrease in wound size) | −10 (10% increase in wound size) |
| Mean % reduction | 69 (69% decrease in wound size) | −38 (38% increase in wound size) |
| Standard Deviation | 14.3 | 80.6 |

TABLE 2

Healing and non-healing leg ulcers.

|  | Healing (n = 20) | Non-healing (n = 32) |
|---|---|---|
| Range | 36 to 98 (Reduction in wound area of 36 to 98%) | −200 to 28 (200% increase in wound area to 28% decrease) |
| Median % reduction | 65 (65% reduction in wound area) | −9 (9% increase in wound area) |
| Mean % reduction | 66 (66% reduction in wound area) | −22 (22% increase in wound area) |
| Standard Deviation | 18.9 | 48.1 |

TABLE 3

Healing and non-healing pressure ulcers.

|  | Healing (n = 3) | Non-healing (n = 7) |
|---|---|---|
| Range | 31 to 77 (Decrease of 31% to 77%) | −100 to 23 (100% increase to 23% decrease) |
| Median % reduction | 55 (55% decrease in wound size) | 5 (5% decrease in wound size) |
| Mean % reduction | 54 (54% decrease in wound size) | −8 (8% increase in wound size) |
| Standard Deviation | 43.0 | 23.0 |

Wound Fluid Collection

For each subject enrolled, two swabs were collected from the wound. Prior to swabbing, the wound was cleansed with sterile saline to remove all loose debris, remains of therapeutic agents (e.g. enzymatic debriders, gels, dressings, etc.) and necrotic tissue. No sharp wound debridement was performed prior to sample collection, and hemostasis was completed before obtaining the specimen. The wound area to be swabbed was moistened with a few (up to five) drops of saline. Swabbing was performed on areas free from blood, necrotic material or thick slough.

Protein Assay

Total protein present in each extracted wound fluid sample was determined using the Bradford protein assay. The protein binding solution comprises 1 ml Coomassie Brillant Blue stock solution 200 mg-Coomassie Brillant Blue G250, Sigma Chemical Co., dissolved in 50 ml ethanol-90%); 2 ml orthophosphoric acid (85% w/v); in a final volume of 20 ml with distilled water. This solution was filtered (Whatman #1 filter paper) and used immediately. The protein level in a sample wound fluid was measured by mixing 10-µl sample or standard with 190-µl of the protein binding solution in a microtitre well and incubating for 30 mins at ambient temperature prior to reading absorbance at 595 nm. The concentration of protein was estimated from a standard calibration of BSA (bovine serum albumin prepared in distilled water; Sigma Chemical Co.) ranging from 1.0 to 001 mg/ml.

Measurement of Human Neutrophil Elastase Activity hNE activity was measured spectrophotometrically using a substrate which mimics the cleavage site of the enzyme. The substrate sequence used was specific for neutrophil derived elastase; MeOSuc-Alanine-Alanine-Proline-Valine-7 amino 4 methyl coumarin (Bachem, Switzerland) (SEQ ID NO: 7). This short peptide substrate also contains the fluorescent reporter group, 7-amino 4-methyl coumarin, which is released upon substrate hydrolysis. Enzyme activity was then calculated by measuring the rate of production of the fluorimetric compound at 450 nm (excitation 380 nm). Activity was expressed as relative fluorescence units per minute and converted to milliunits of elastase activity per minute per 110 µL swab extract (mU/min/110 µL) from a standard curve.

The substrate, MeOSuc-Alanine-Alanine-Proline-Valine-7 amino 4 methyl coumarin (SEQ ID NO: 7) shows good specificity to human elastase. *Pseudomonas aeruginosa* elastase is not able to cleave the peptide, demonstrating that there is no cross reactivity with the bacterial elastase. Although the substrate is most susceptible to cleavage by elastase, it can also be cleaved to a much lesser extent by Proteinase 3, a neutrophilic protease with similar substrate specificity to Elastase.

Measurement of Matrix Metalloproteinase (MMP) activity

Matrix metalloproteinase (MMP) activity was measured spectrophotometrically using a substrate which mimics the cleavage site of the enzyme. The substrate sequence used was specific for MMP activity; Mca-Lys-Pro-Leu-Gly-Leu-Dpa-Ala-Arg-NH$_2$. TFA [Mca=(7-methoxycoumarin-4-yl) acetyl; Dpa=N-3-(2,4-dinitrophenyl)-L-α,β-diaminopropionyl] (Enzo Life Sciences) (SEQ ID NO:12). This peptide substrate contains the fluorescent reporter group 7-methoxycoumarin-4-yl) acetyl, which is released upon substrate hydrolysis. Enzyme activity was then calculated by measuring the rate of production of the fluorimetric compound at 400 nm (excitation 328 nm). Activity was expressed as relative fluorescence units per minute and converted to units of MMP activity per minute per 110 µL swab extract (U/min/110 µL) from a standard curve.

Data Analysis

A total of 93 samples were analysed using Microsoft Excel and Minitab 16 in order to:

(a) Review the distributions of quantitative data and consider possible data transformations;

(b) Examine interactions between measured levels of the specific protease;

(c) Obtain graphical representation of potential regression between Healing and Non-healing quantitative protease measured data; and (d) Review the application of Binary Logistical Regression as a potential model.

All four data sets [(hNE, healing) (hNE, non-healing) (MMP, healing) (MMP, non-healing)] have a large negative skew, and given the number of observations in each data set (n=36 n=57* n=36 n=57* respectively) then an assumption of normality cannot be made. [* on the advice of researchers one data point was omitted as being invalid as sample was taken earlier than standard period]. Standard transformations had marginal affect on degree of skewness and more extreme approaches were delayed until further evaluations made this to be considered necessary.

Scatter graphs of hNE vs MMP at both categories showed limited evidence for a correlation between the two parameters (see FIGS. 4 and 5) and non-correlation has been assumed.

Scatter diagrams for both protease measurements with category showed an overlapping distribution and hence a potential regression fit using a logistical approach was considered.

Using Minitab 16 and Stats/regression/binary logistical a logistical model was evaluated. High leverage points on hNE (n=1) and MMP (n=2) were omitted from the models before reanalysis. Diagnostic indicators showed no reason to discount the model and without a further detail assessment or data transformation an expected distribution was obtained for both hNE and MMP measurement. This is summarised below.

hNE Activity

| Reported Result mU/100u | Estimated Probability of Non-healing Wound | Standard Error | CI (95%) |
| --- | --- | --- | --- |
| 17 | 0.80 | 0.08 | (0.62, 0.93) |
| 25 | 0.90 | 0.08 | (0.66, 0.98) |
| 33 | 0.95 | 0.05 | (0.70, 0.99) |
| 55 | 0.99 | 0.02 | (0.78, 1.0) |

MMP Activity

| Reported Result U/100u | Estimated Probability of Non-healing Wound | Standard Error | CI (95%) |
| --- | --- | --- | --- |
| 32 | 0.80 | 0.08 | (0.61, 0.92) |
| 48 | 0.90 | 0.07 | (0.65, 0.98) |
| 64 | 0.95 | 0.05 | (0.69, 0.99) |
| 100 | 0.99 | 0.02 | (0.76, 1.0) |

Figure 4:
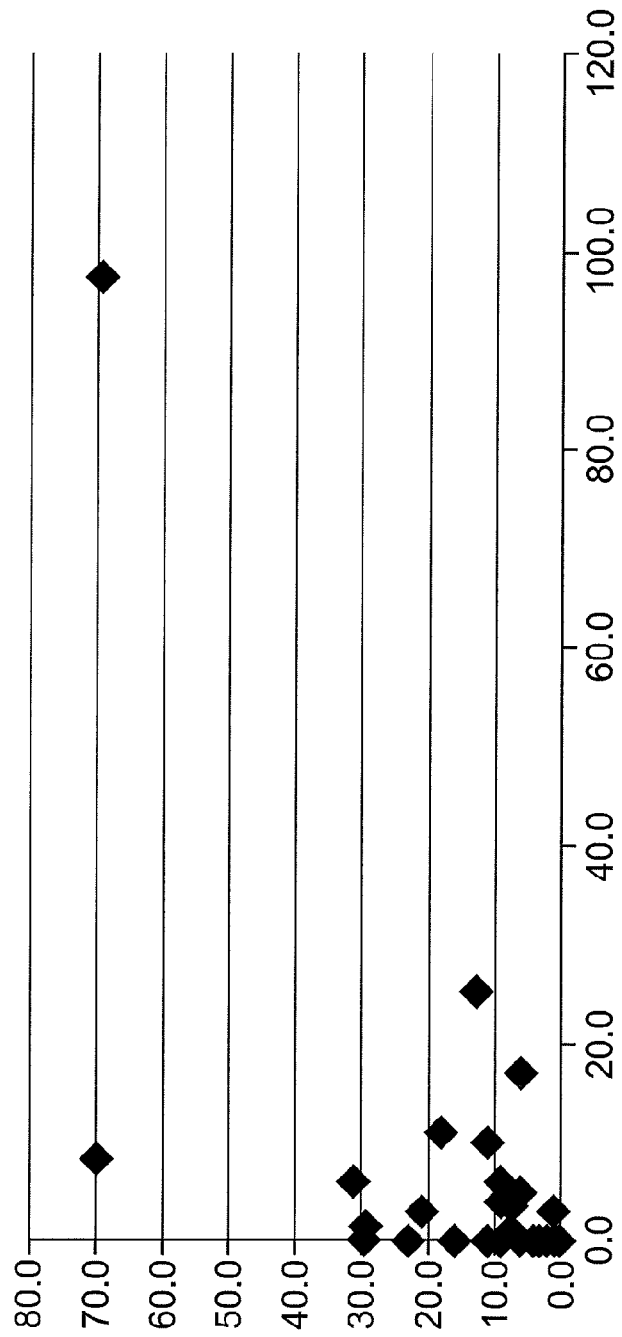
FIG. 4 shows a graph of measured hNE versus MMP activity in healing wounds.
Figure 5:
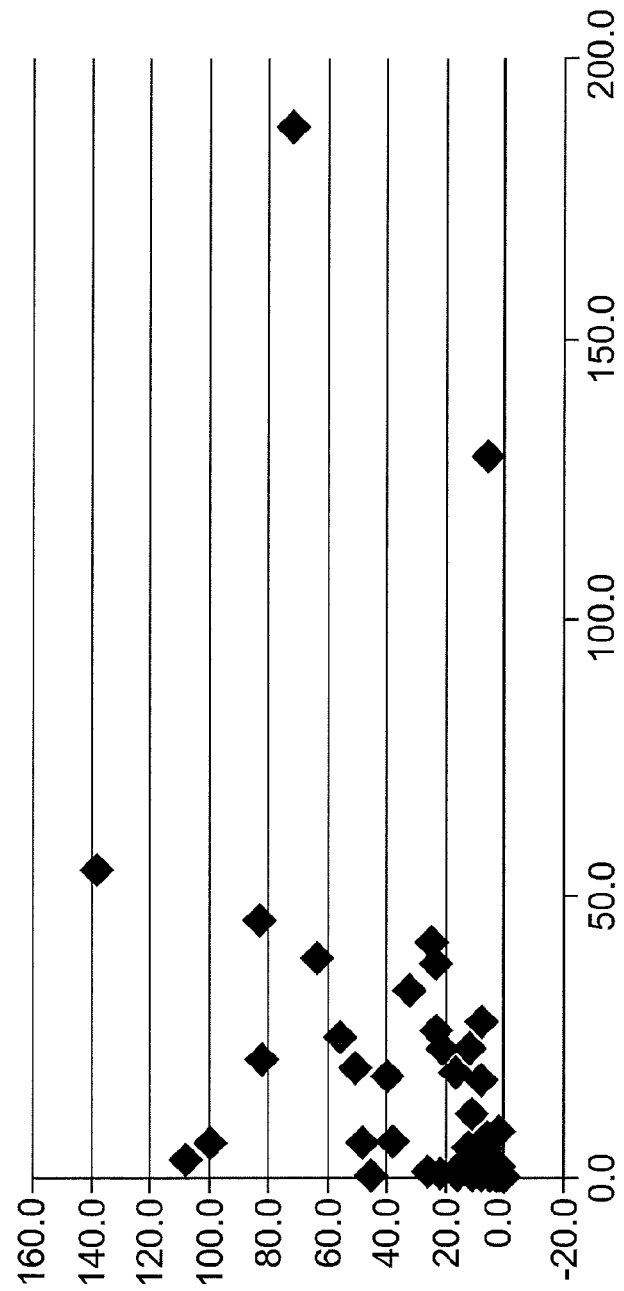
FIG. 5 shows a graph of measured hNE versus MMP activity in non-healing wounds.

The statistical report concluded that there was limited evidence for any correlation between the two reference assay results. FIG. 4 shows a scatter diagram of protease activity in healing and non-healing wounds, some wounds have elevated levels of MMP activity but low levels of hNE activity, and vice versa. This may be due to the fact that several proteases can degrade the same substrates, so they may be able to compensate for each other, also, different wounds may have different profiles of elevated protease activity depending on the stage of the inflammatory response. Therefore the reference assays have been given individual thresholds, so if the protease activity is above either the hNE activity or the MMP activity threshold it will be classed as having elevated protease activity.

The results obtained from the application of a Binary Logistical Regression model provided an estimate of the probability of a wound being Non-healing for any given value of measured Protease activity levels. The Binary Logistical model can be used to provide a probabilistic estimate of the categorisation of the wound (healing or non-healing) based upon measured levels of protease enzyme activity obtained from wound fluids. The model can be used to calculate the thresholds of hNE activity and MMP activity that would be required for any given probability that is applied to the model. We have applied a 0.90 estimated probability of non-healing, this sets the thresholds at a value of 25 mU/1104 for hNE activity and 48 U/1104 for MMP activity. That means that there is a 90% probability that any sample which is over 25 mU/110 µL hNE and/or 48 U/1104 MMP is a non-healing wound with elevated protease activity.

Figure 6:
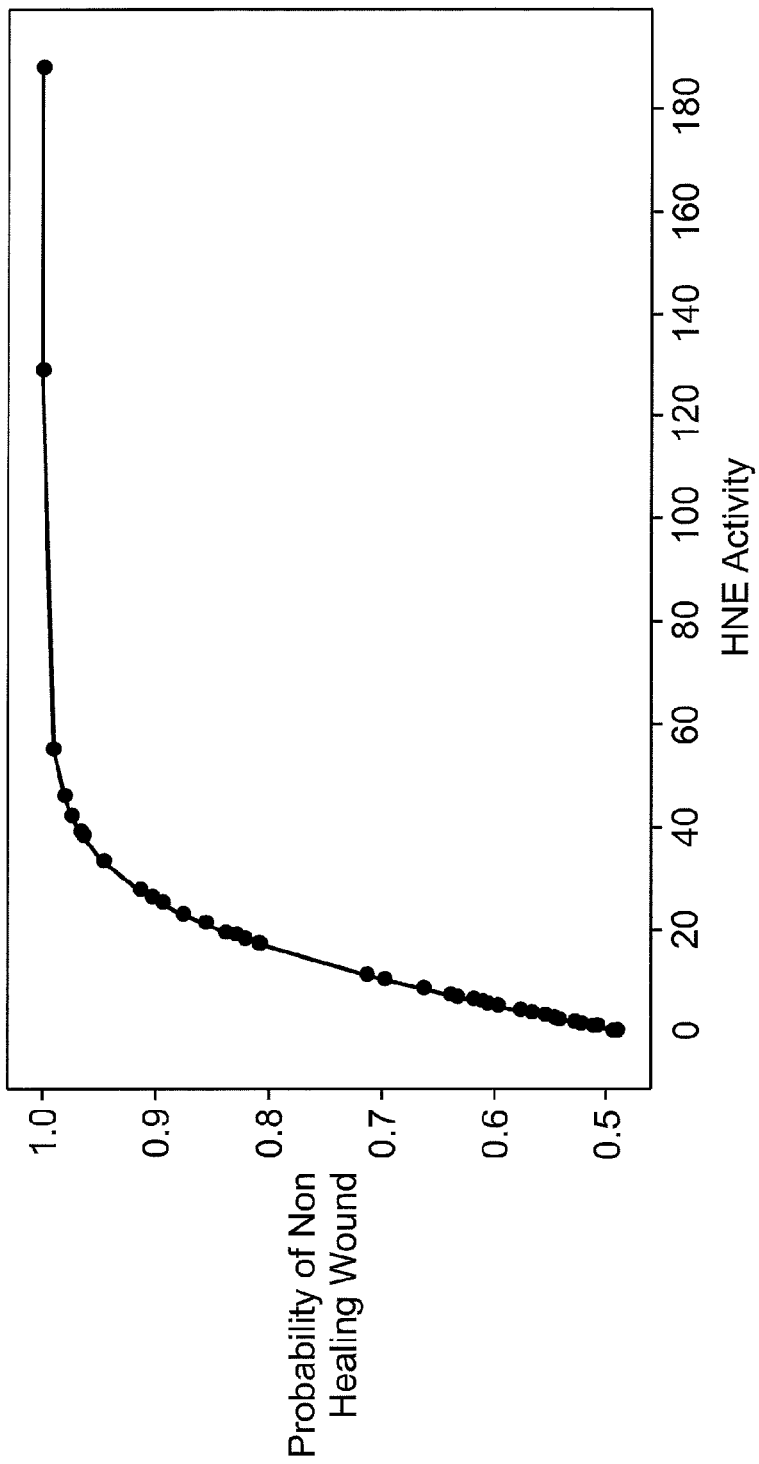
FIG. 6 shows a graph of the probability of a wound being non-healing versus measured hNE activity for a population of healing and non-healing wounds.
Figure 7:
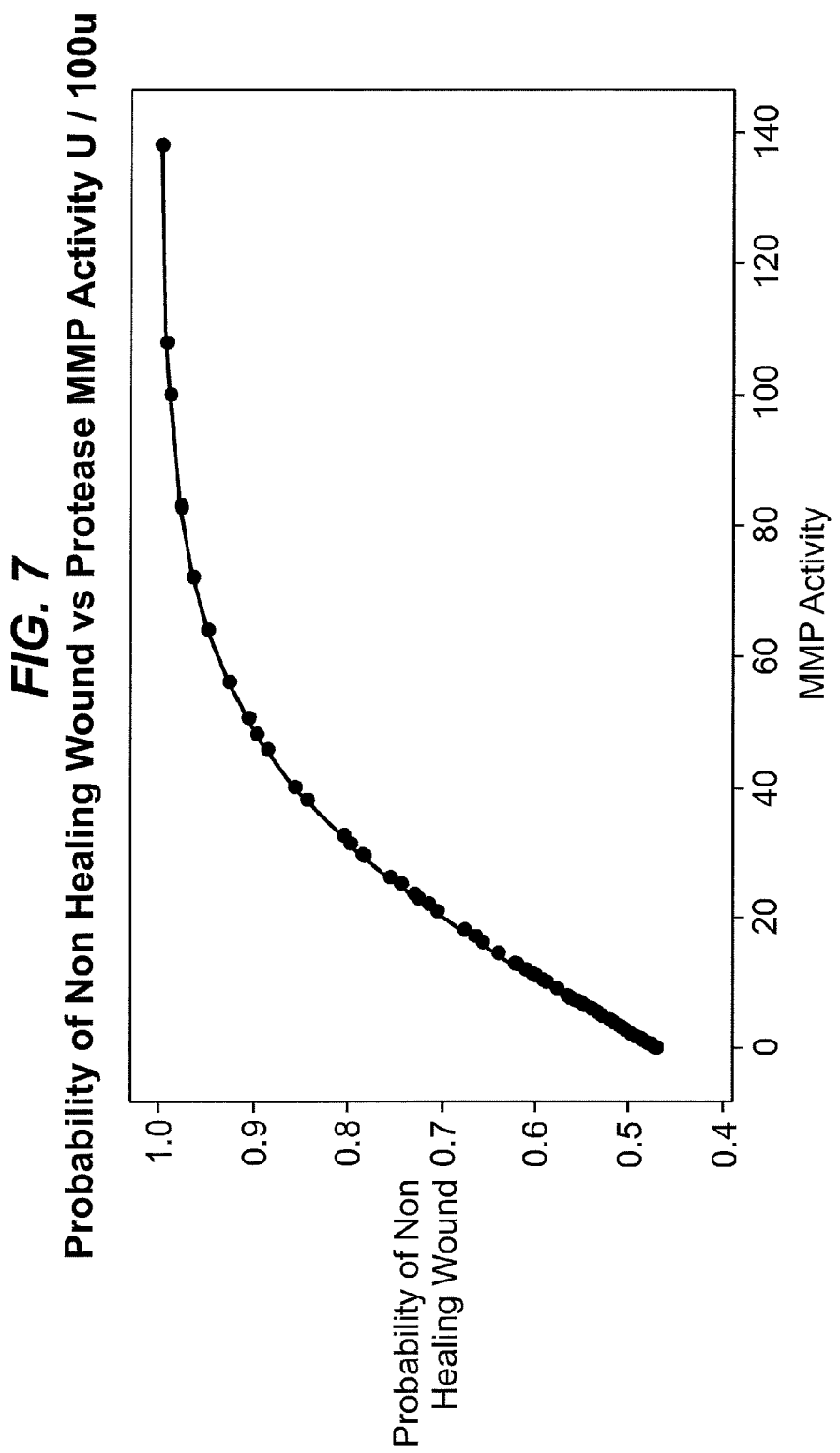
FIG. 7 shows a graph of the probability of a wound being non-healing versus measured MMP activity for a population of healing and non-healing wounds.

Based on the data 12.9% of wounds would be over these thresholds and the positive predictive value (PPV) for non-healing wounds is 83.3%. FIGS. 6 and 7 shows the hNE and MMP activity versus cumulative probability of non-healing wounds.

Device/Apparatus According to Aspects of the Present Invention

Referring to FIGS. 8-10, the folding card device 2 according to the present invention comprises front and back flaps 3,4 of cartonboard material joined by a living hinge 5. A strip 6 of pressure sensitive adhesive on the back flap 4 provides a retaining element for retaining edge 7 of the front flap when the card device is folded shut. The adhesive strip 6 is covered by a releasable cover sheet (not shown) that is removed immediately before use. A lateral flow test strip 8 is mounted on the inside surface of the front flap 3, for example by adhesive. A thermoformed plastic swab well 10 is mounted in the back flap 4 and partially covered by a cover sheet 12 having apertures 14,16 located respectively above upper and lower regions of the plastic swab well 10. The swab well 10 contains dry reagents 11 as described further below. The aperture 16 is located such that, when the card is folded shut, the aperture 16 abuts a sample receiving region 13 of the test strip 8, but aperture 14 does not abut the test strip 8.

A window 9 in the front flap 3 is located over a region of the test strip where the sample and control read-out lines are located, so that this region of the test strip can be viewed when the card is folded shut. One or more reference colour areas 15 may be printed on the outside of the front flap 3 for comparison with a colour displayed in the read-out lines.

In use, the swab well 10 is primed by the addition of a few drops of a wash liquid, for example a saline solution. A swab having a sample of wound fluid is inserted into the swab well 10 through the aperture 14 and rotated to release the sample into the wash liquid in the well. The card is then folded shut and secured shut with the adhesive strip 6. The swab is usually attached to a swab shaft or stick 17, which can project out of the bottom of the closed card device. When the card is shut, the liquid containing the sample passes through the aperture 16 by capillary action into a sample receiving region 13 of the test strip 8. The user may be instructed to allow the reagents in the swab well to react with the sample for a predetermined time, e.g. 10 minutes, before closing the card.

Referring to FIGS. 11-14, lateral flow test chemistry similar to that described in WO2007/128980 is used in this embodiment. The swab well 10 contains colloidal gold particles 20 conjugated to antibody 22 that is selective for a binding partner that is immobilized on the control line of the test strip as explained further below. The colloidal gold particles are sized such that they exhibit a red coloration when dispersed in a liquid or solid matrix. The swab well 10 further comprises the peptide substrate 24 for the analyte protease(s) conjugated to biotin 26.

Referring to FIG. 15, the test strip 8 comprises a sample receiving area 28 of blotting paper or similar absorbent sheet material, a porous area 29 impregnated with colloidal gold 20 conjugated to an antibody specific for the peptide substrate 24, a test area 30, and an absorbent reservoir area 32 for drawing the liquid through the test area 30 by capillary action. The test area comprises a sample read-out band 31 in which the test area substrate is conjugated to polystreptavidin 34, and a control read-out band 33 in which the test area substrate is conjugated to an antigen 35 that binds strongly to the antibody 22 on the colloidal gold particles from the swab well.

Referring to FIG. 13, the operation of the device when the sample does not contain protease analyte is shown. In the absence of protease analyte in the sample, the cleavable peptide moiety 24 to binds strongly to the conjugate antibody on the colloidal gold particles of the test strip, thereby forming a complex comprising the colloidal gold 20 joined to the biotin 26. This complex binds to the streptavidin in the sample read-out band, thereby producing a red colour in this band due to the presence of the colloidal gold. The other gold conjugate from the swab well binds to the antigen in the control read-out band of the strip, thereby producing a red colour in this band due to the presence of the colloidal gold. Therefore, a red line in both the sample band and the control band signifies that the test has been performed successfully, but that the amount of analyte protease in the sample is below the threshold used to define a 90% probability of non-healing wounds.

Referring to FIG. 14, the operation of the device when the sample contains protease analyte is shown. The addition of the protease analyte to the swab well 10 causes the cleavable peptide moiety 24 to be cleaved by the protease analyte. The cleavage fragments do not bind strongly to the conjugate antibody on the colloidal gold particles of the test strip, and therefore binding of the colloidal gold 20 to the biotin 26 does not take place. As a result, little or none of the gold binds to the streptavidin in the sample read-out band, thereby producing little or no red colour in this band due to the presence of the colloidal gold. The other gold conjugate from the swab well still binds to the antigen in the control read-out band, thereby producing a red colour in this band due to the presence of the colloidal gold. Therefore, a red line in only the control band signifies that the test has been performed successfully, and that the amount of analyte protease in the sample is above the threshold characteristic of non-healing wounds. This is as an indication of a non-healing wound.

Specific wound dressing materials and methods according to a number of aspects and embodiments of the present invention and suitably relating to determining the likelihood of a wound responding to treatment with therapy such as oxidized cellulose therapy (i.e. whether responsive or non-responsive) will now be described further with reference to the accompanying drawings, which are described above.

Preparation of the Wound Dressing Component

The collagen/ORC sponge dressing used in these studies was commercial PROMOGRAN PRISMA™ (Systagenix Wound Management) dressing prepared substantially as described in EP-A-1536845.

Promogran Prisma is a 2% solids, freeze-dried matrix consisting of 55% Bovine Collagen, 44% Oxidised regenerated cellulose fibres (ORC) and 1% silver- ORC salt (silver acetate). To prepare the dressing ORC and silver ORC fibres are added to 0.05M acetic acid solution and mixed until evenly dispersed. To this suspension, Bovine collagen, approximately 1% solids, are added and the preparation is mixed and passed through a homogeniser to obtain a uniform slurry. The preparation is then poured into trays and freeze dried to remove the excess acetic acid and water so that the bioresorbable matrix is left behind. This is then slit to a thickness of 3 mm and cut into dressing of 28 or 125 $cm^2$, prior to gamma sterilisation.

Clinical Study and Patient Selection

All patients enrolled in this study had diabetic foot ulcers of at least 30 days duration and a surface area of at least 1 $cm^2$. Specific inclusion criteria are disclosed below:

Inclusion Criteria

The patient must:

Have diabetes

Be aged between 35 to 80 years

Show no local or systemic signs of infection with normal CRP and leukocyte levels and defined as being DFU type Wagner 2-3 (>4 weeks old).

Have an ulcer of at least 30 days duration.

Be willing to return to the investigation centre for all dressing changes and wound evaluation.

Be willing to give written informed consent.

Patients were excluded if the target wound showed any signs of infection or if exposed bone with positive osteomyelitis was observed. Additional exclusion criteria included concomitant conditions or treatments that may have interfered with wound healing and a history of non-compliance that would make it unlikely that a patient would complete the study. Specific exclusion criteria are disclosed below:

Exclusion Criteria

The patient must not:

Exhibit allergic reactions to any content of Promogran Prisma

Have clinical signs of infection as defined by clinicians

Be pregnant or lactating

Have a history of misuse of drugs or excessive alcohol consumption

Be undergoing chemotherapy

Have peripheral arterial disease and/or toe pressure ≤45 mm. Hg

Have haemolytic anemia and/or iron-deficiency anemia and/or malnutrition.

Be able to walk.

Have severe cardiac and/or hepatic and/or renal and/or pulmonary insufficiency; or chronic administration of cortisones for chronic inflammatory disease and/or auto-immune disease. The wound must not be considered malignant.

Patients meeting the patient selection criteria disclosed above were enrolled (exact numbers for each assay method are disclosed below), and wound fluid collected. Informed consent was obtained from all patients or their authorised representatives prior to study enrolment and the protocol was approved by the Ethics Committee at the participating study centre prior to the commencement of the study. The studies herein were conducted in accordance with both the Declaration of Helsinki and Good Clinical Practice.

Wound Fluid Collection and Extraction from Dressings

Wound fluid was collected by absorption onto a piece of RELEASE* dressing, which was placed directly onto the wound and covered with BIOCLUSIVE, an occlusive film. These dressings are commercially available from Systagenix Wound Management Manufacturing Limited.

RELEASE* Non-Adherent Absorbent Dressing consists of a labeled, sterile pouch containing a rectangular web of viscose rayon fibres sandwiched between layers of non-woven fabric in a sleeve of perforated EMA film, which is sealed by a line of hot melt adhesive.

BIOCLUSIVE® is a hypoallergenic, transparent, adhesive film dressing with a three-part release coated facing paper which is impermeable to water and bacteria and permeable to moisture and oxygen. The dressings are designed for easy aseptic application through the use of three removable facing tabs. The facing tabs are bleached paper, coated on one side with polyethylene that is then covered by a silicone coating.

After 24 hours the dressing was removed from the wound and frozen at −70° C. until elution of wound fluid.

Wound fluid was eluted from the RELEASE* dressing by incubating the sample in 5-10 mL of wash buffer (0.1 M Tris/HCl, pH 7.4 containing 0.1% Triton X-100) per gram of dressing depending on surface area of the dressing to minimise the dilution of the wound fluid. To allow maximum recovery of fluid, the sample was incubated for 2 hours at room temperature with shaking. The eluent was then carefully removed, aliquoted and frozen at −70° C. until required for use.

Example 1

Determining the Amount of Elastase by Fluorogenic Activity Assay

A fluorogenic substrate, MeOSuc-Ala-Ala-Pro-Val-AMC (BaChem) (SEQ ID NO: 7) which is cleaved by elastase to release the fluorogenic group 7-amino-4-methylcoumarin was used to measure elastase activity in the wound fluid samples.

The wound fluid samples were added to a black, flat bottomed microtitre plate. The final reaction mixture consisted of 5 µL of wound fluid, 175 µL of elastase assay buffer (0.1 M hepes, 0.5 M sodium chloride, 10% dimethylsulphoxide, pH 7.5) and 20 µL substrate, which was added to a final concentration of 0.2 mM per well.

Using a fluorometer (excitation 380 nm, emission 450 nm) readings were taken immediately after addition of the substrate and then after 5, 10, 15, 20, 30, 45 and 60 minutes. The plate was incubated at 37° C. between readings. The rate of production of the fluorescent compound was measured, (fluorescence directly relates to elastase activity in the sample). The results were expressed as relative fluorescence units per minute per mL (RFU/min/mL).

Example 2

Determining the Amount of Matrix Metalloproteinase by Protein Microarray

MMP-1 and MMP-9 in wound samples were quantified using FAST Quant protein microarray (commercially available from Whatman).

Different sets of arrays were printed on 16-pad FAST slides in triplicates using a piezo-electric Perkin-Elmer BioChip Arrayer. The arrays consisted of monoclonal antibodies against a variety of cytokines (up to 11 different cytokines were quantified per array). Arrayed slides were then inspected and stored in a desiccated room until required.

Prior to analysis, the slides were removed from storage and a 16-pad hybridization chamber was attached to the slides, and the slides were placed into a FAST Frame (4 slides per frame) for processing.

Arrays were blocked for 15 minutes at room temperature using 70 µL S&S Protein Array Blocking buffer. The blocking buffer was removed and 70 µL of each wound fluid sample (at a 1:20 or 1:50 dilution), standard or control was added.

Arrays were incubated overnight at room temperature, with gentle agitation and then washed 5 times with TBS-T.

Arrays were treated with 70 µL of an antibody cocktail, containing one biotinylated antibody corresponding to each of the arrayed capture antibodies. Following 1 hour incubation at room temperature with gentle agitation, the arrays were washed 5 times with TBS-T.

Arrays were incubated with 70 µL of a solution containing streptavidin-Cy5 conjugate for 1 hour at room temperature, with gentle agitation. Arrays were washed 5 times with TBS-T, quickly rinsed in de-ionized water, and dried.

Slides were imaged in an Axon GenePix 4000B fluorescent imaging system. Array images were saved as 16-bit TIF files, with 10 micron pixel resolution. Images were analyzed using Imaging Research ArrayVision software. Briefly, spot intensities were determined by subtracting background signal. Spot replicates from each sample condition were averaged and then compared to the appropriate standard curves. Microsoft Excel was used for additional analysis and data presentation. The quantified amounts of MMP-1 and MMP-9 were provided in units of ng/mL.

Example 3

Protein Assay

Total protein present in each extracted wound fluid sample was determined using the Bradford protein assay. The protein binding solution comprises 1 ml Coomassie Brillant Blue stock solution 200 mg-Coomassie Brillant Blue G250, Sigma Chemical Co., dissolved in 50 ml ethanol-90%); 2 ml orthophosphoric acid (85% w/v); in a final volume of 20 ml with distilled water. This solution was filtered (Whatman #1 filter paper) and used immediately. The protein level in a sample wound fluid was measured by mixing 10-µl sample or standard with 190-µl of the protein binding solution in a microtitre well and incubating for 30 mins at ambient temperature prior to reading absorbance at 595 nm. The concentration of protein was estimated from a standard calibration of BSA (bovine serum albumin prepared in distilled water; Sigma Chemical Co.) ranging from 1.0 to 001 mg/ml.

Example 4

Wound Sampling

Twenty six patients meeting the patient selection criteria disclosed above were enrolled, and wound fluid collected. Wound fluid was collected again after four weeks.

The amount of elastase-like activity (as indicated by the method of Example 1), MMP-1 and MMP-9 (as indicated by the method of Example 2) in the wound fluid of each patient was analysed immediately before wound treatment commenced.

Eighteen of the twenty six patients were then treated by application of PROMOGRAN PRISMA™ dressing to the whole surface of the ulcer, together with suitable secondary dressings to hold the PROMOGRAN PRISMA™ in place. The remaining eight control patients received "good standard care". Patients were treated with a range of different dressings, including:

| Dressing | Manufacturer | Brief description |
| --- | --- | --- |
| Physiotulle | Coloplast | Physiotulle is a non-adherent, non-occlusive polyester net impregnated with hydrocolloid particles suspended in Vaseline. |
| Physiotulle Ag | Coloplast | non-adherent, moist wound healing contact layer with silver sulphadiazine |
| Biatain-Ibu | Coloplast | foam dressing which releases ibuprofen. |
| Mesorb | Molnlycke Health Care Ltd | Mesorb is made of two layers of a permeable, smooth nonwoven which ensures good skin compatibility and exudate permeability. The soft, thick fluff pulp core combines excellent absorption capacity with good protective cushioning and the air-permeable and fluid-repellent nonwoven backing provides an excellent exudate barrier. |
| Silver dressing Silver Gauze Foam dressing Silver alginate | Information not available | |

The wound fluid from each patient was sampled again after four weeks in the same manner as disclosed above. Patients who developed symptoms of infection, or whose treatment was discontinued for other reasons, were excluded from the study.

All patients completed the trial to week 4. However, wound analysis could not be completed for three of these patients due to low abundance of wound fluid.

The groups of patients receiving treatment in this trial could be divided into two sub-groups of patients:
a) Responders, i.e. patients whom exhibited better than 50% wound closure after 4 weeks of treatment; and
b) Non-responders, i.e. patients whom exhibited less than 50% wound closure after 4 weeks of treatment.

Experimental Data Analysis

Figure 16:
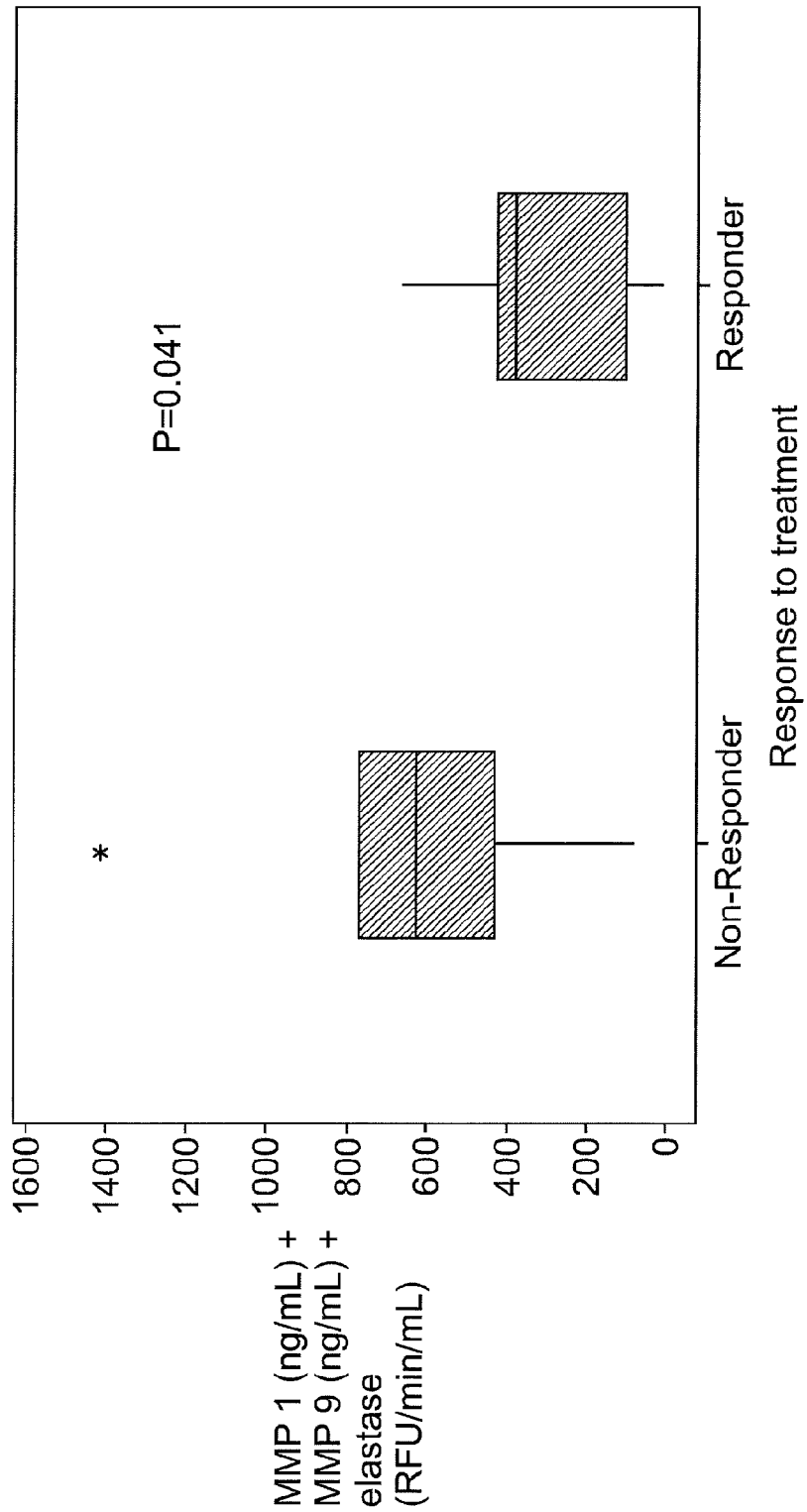
FIG. 16 provides a box plot analysis of the sum of elastase-like activity (RFU/min/mL), MMP-1 concentration and MMP-9 concentration (ng/mL) in wound exudate taken from patients before the wound treatment program as described in Example 4 commenced, i.e. at week 0. The data is grouped to identify patients who responded well to wound treatment (i.e. responders (R)) and those patients who did not respond well to treatment (i.e. non-responders (NR)) as defined in Example 4. The data show a significant difference (p<0.05) between the sum of these proteases in responders compared to non-responders before treatment.

The sum amounts of elastase-like activity, MMP-1 concentration and MMP-9 concentration in responders (R) before wound treatment (i.e. week 0) with PROMOGRAN PRISMA™ are compared with the corresponding data obtained from non-responders (NR) in the box plots in FIG. 16. Elastase-like activity was calculated as RFU/min/mL according to Example 1. Both MMP-1 and MMP-9 were calculated in ng/mL according to Example 2, above.

When testing was carried out, certain values were over or under the maximum range that the assay could detect. The samples that were "under" were allocated a value of 0. For the samples that were "over", the highest point in the data set was taken and rounded up to the nearest thousand. This value was then given to all values found to be "over" the maximum range that the assay could detect.

Figure 17:
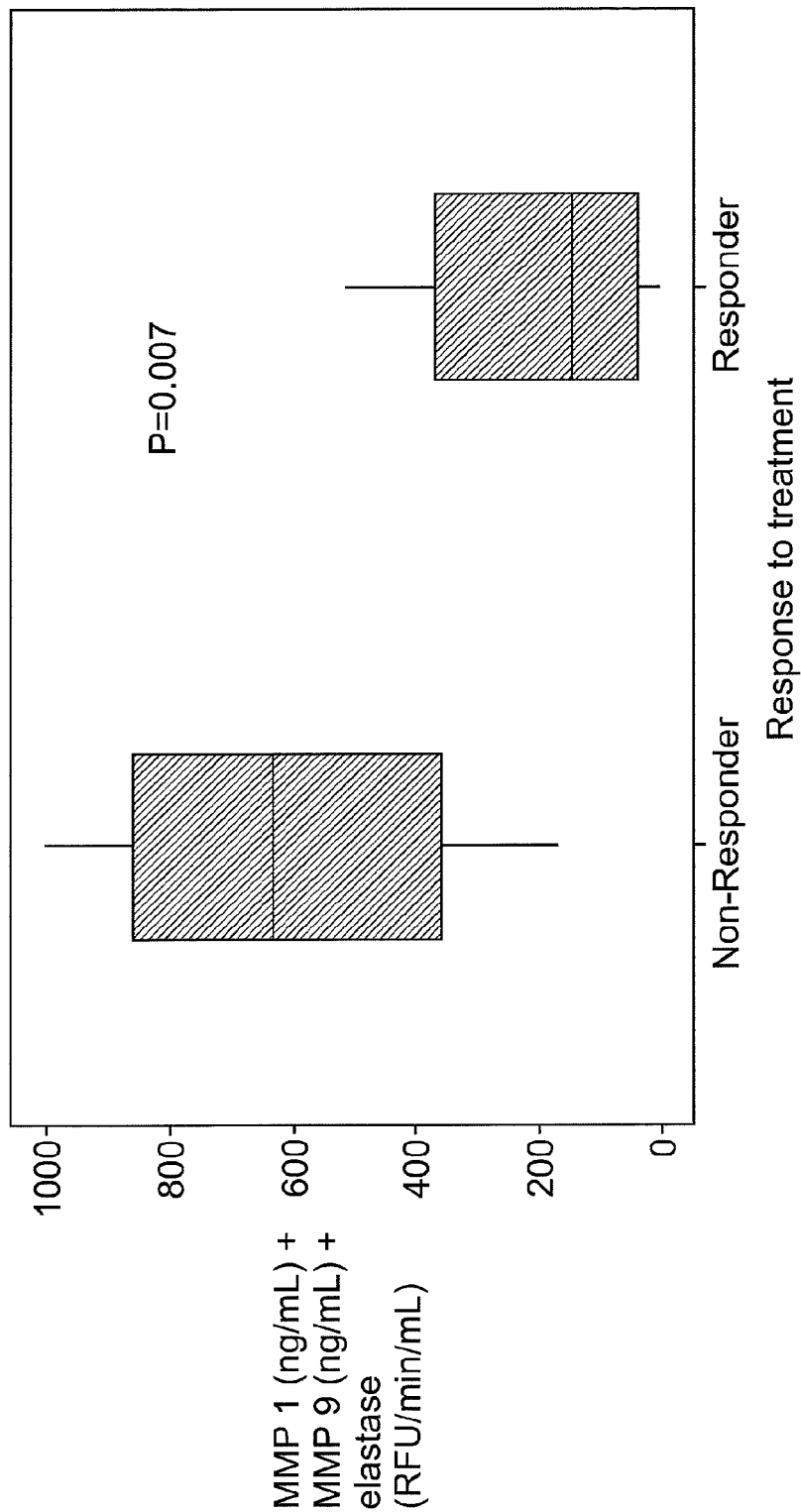
FIG. 17 provides a box plot analysis of the sum of elastase-like activity (RFU/min/mL), MMP-1 concentration and MMP-9 concentration (ng/mL) in wound exudate taken from patients after week 4 of the wound treatment program as described in Example 4. The data show a significant difference (p<0.05) between the sum of these proteases in responders compared to non-responders after treatment.

The sum amounts of elastase-like activity, MMP-1 concentration and MMP-9 concentration in responders (R) after week 4 of wound treatment are compared with the corresponding data obtained from non-responders (NR) in the box plots in FIG. 17. Elastase, MMP-1 and MMP-9 were calculated as described above.

Minitab statistical analysis programme was used for all statistical analysis of these data. A 2 sample t test was used for statistical analysis and differences were considered significant if $p<0.05$. The sum amounts of elastase, MMP-1 and MMP-9 as determined above were normally distributed. However, when data was not normally distributed, a Johnson transformation using the Minitab statistical analysis programme was used before the t test. Where the data could not be transformed, a Kruskal-Wallis test was used using the Minitab statistical analysis programme.

The box plots illustrated in FIG. 16 clearly show that there is, surprisingly, a statistically significant difference ($p=0.041$) between the sum amount of elastase-like activity, MMP-1 and MMP-9 in responders before commencement of wound treatment (i.e. at week 0). The data in FIG. 2 also confirms that this difference is also present after treatment (i.e. at week 4).

In particular, the combined amount of elastase, MMP-1 and MMP-9 in the wound fluid of the responders before treatment with oxidised cellulose dressing was significantly lower than the combined amounts of these proteases in the wound fluid of non-responders.

Accordingly, from these data it can be concluded that the amount of elastase, MMP-1 and MMP-9 in wound fluid is a particularly clear and reliable prognostic tool for identifying wounds that will benefit most from therapy with oxidized cellulose and to identify those that are benefiting from therapy with oxidized cellulose.

Reference Example 1

Total Protein Concentration

Figure 18:
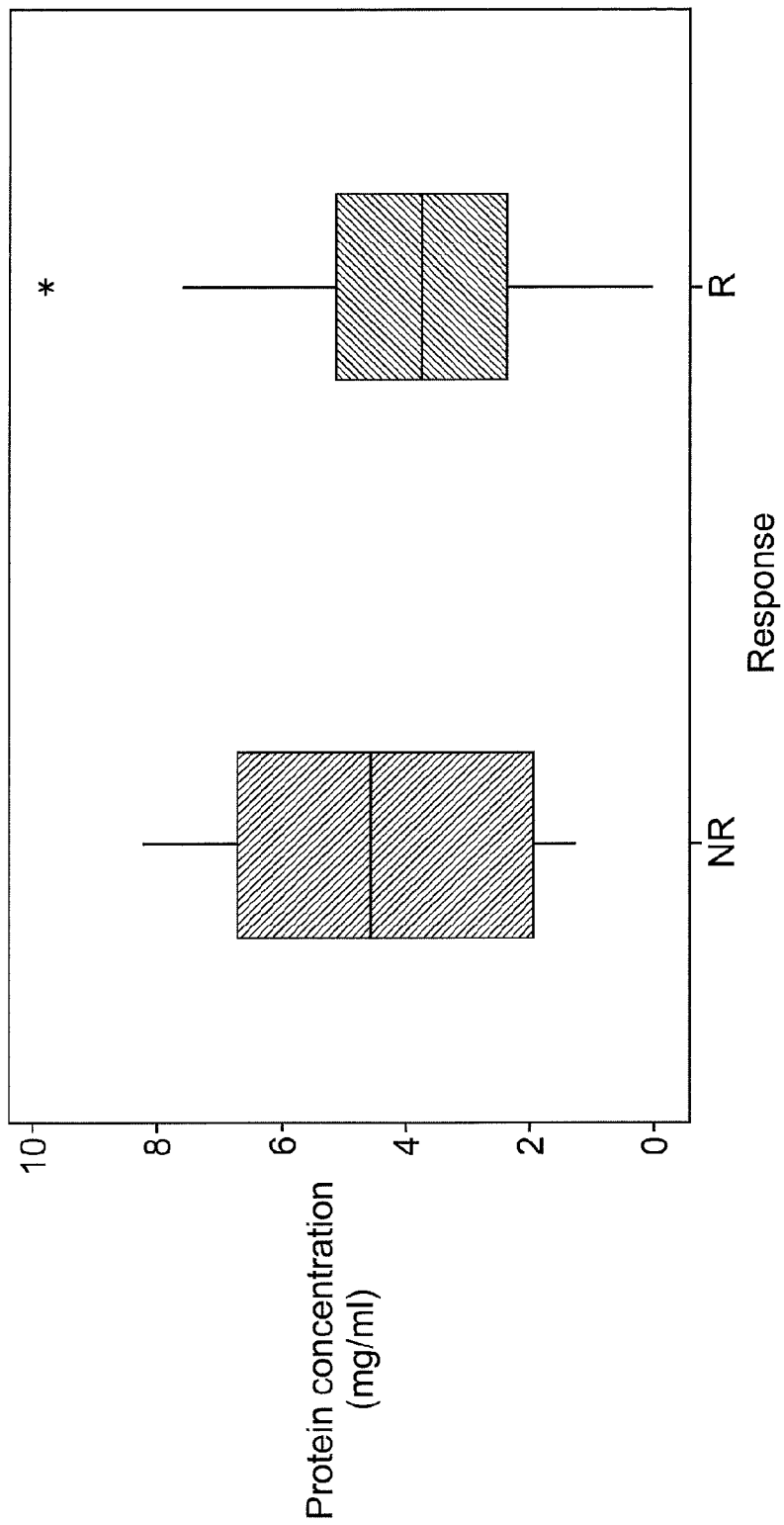
FIG. 18 provides a box plot analysis of the total protein concentration in samples of wound fluids taken from patients before the wound treatment program as described in Example 4. The data show no significant difference between the total protein concentrations in responders compared to non-responders before treatment.

The total amount of protein in wound samples of the patients was determined according to the method of Example 3, above. The data are presented as a box plot in FIG. 18 and clearly show that before treatment with oxidised cellulose commenced (i.e. at week 0), there was no significant difference between total protein concentration in patients identified as responders and those identified as non-responders (responders and non-responders are as defined in Example 4). Accordingly, the total protein concentration of a sample of wound fluid before treatment with oxidised cellulose is not a useful indicator of the likelihood that the wound would respond well to said treatment.

Reference Example 2

Elastase Activity

Figure 19:
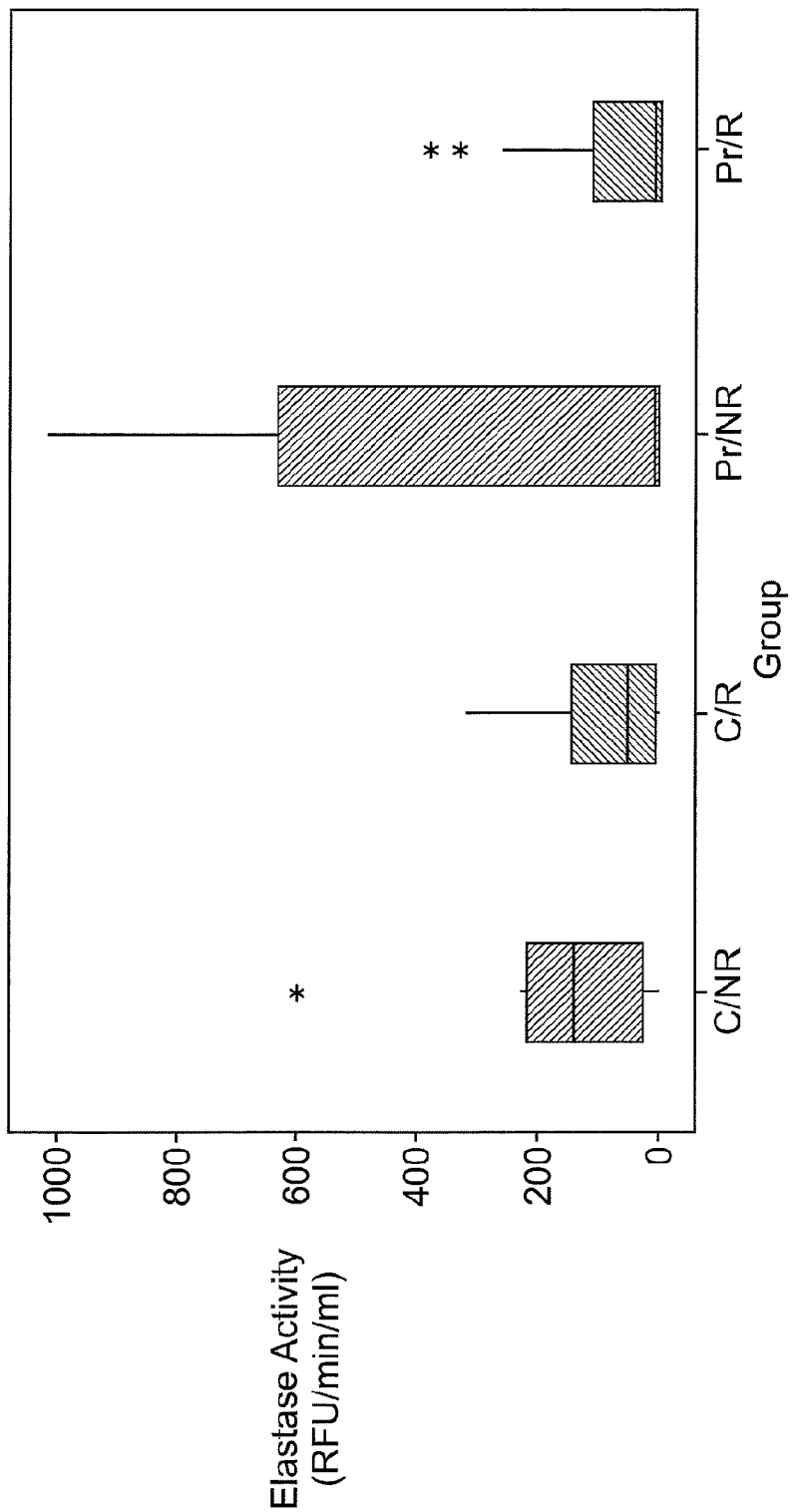
FIG. 19 provides a box plot analysis of the elastase activity in samples of wound fluids taken from patients before the wound treatment program as described in Example 4. The data show no significant difference between the elastase activities in responders compared to non-responders before treatment.

The activity of elastase alone in wound samples of the patients was determined according to the method of Example 1, above. The data are presented as a box plot in FIG. 19 and clearly show that before treatment with oxidised cellulose commenced (i.e. at week 0), there was no significant difference between elastase activity in patients identified as responders and those identified as non-responders (responders and non-responders are as defined in Example 4). Accordingly, the activity of elastase alone in a sample of wound fluid before treatment with oxidised cellulose is not a useful indicator of the likelihood that the wound would respond well to said treatment.

Reference Example 3

MMP-1 Concentration

Figure 20:
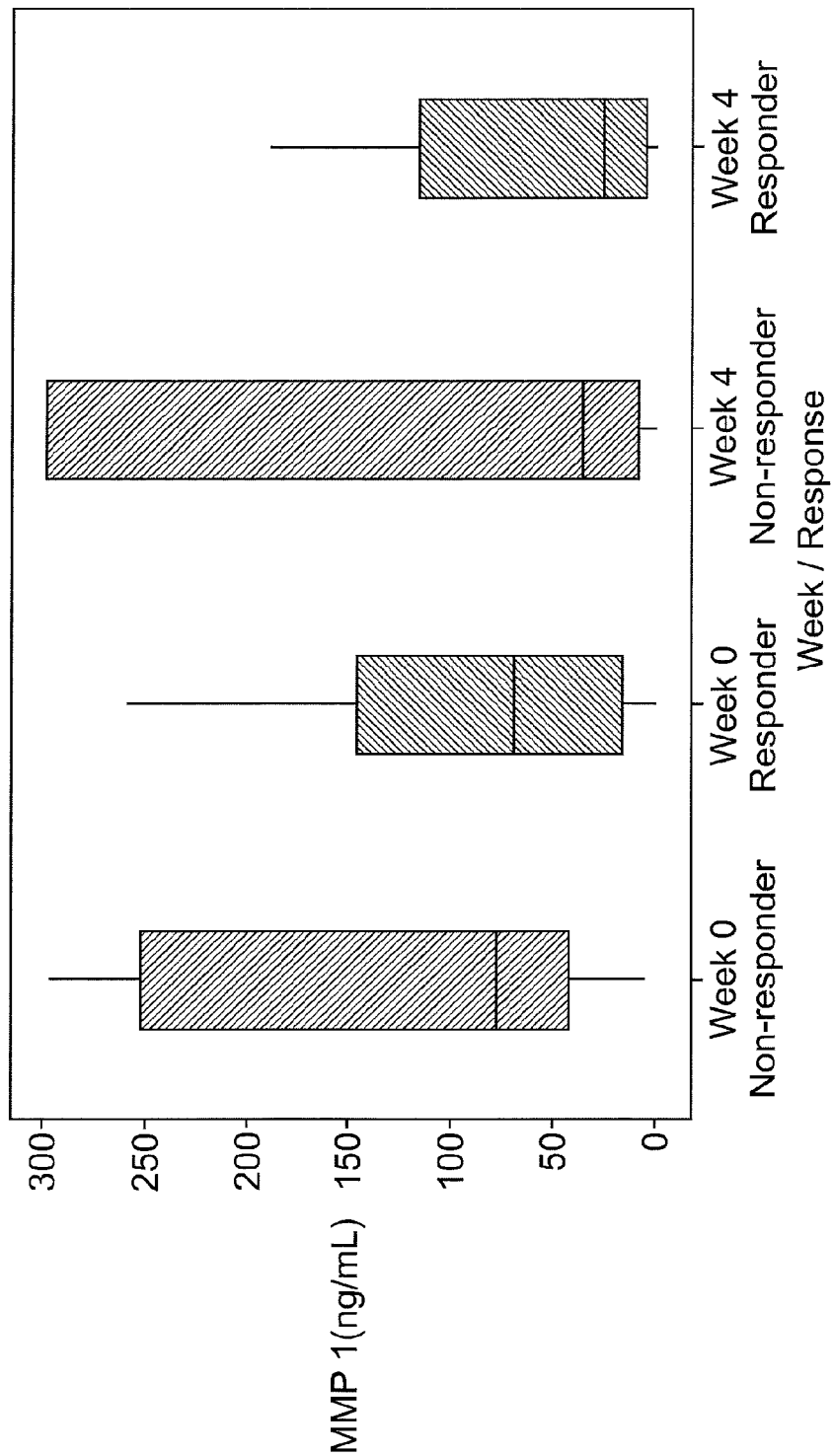
FIG. 20 provides a box plot analysis of the concentration of MMP-1 in samples of wound fluids taken from patients before and after the wound treatment program as described in Example 4. The data show no significant difference between the concentrations of MMP-1 in responders compared to non-responders before (week zero, p=0.438) or after (week four, p=0.688) treatment.

The concentration of MMP-1 alone in wound samples of the patients was determined according to the method of Example 2, above. The data are presented as a box plot in FIG. 20 and clearly show that before treatment with oxidised cellulose commenced (i.e. at week 0), there was no significant difference between MMP-1 concentration in patients identified as responders and those identified as non-responders (responders and non-responders are as defined in Example 4). Accordingly, the amount of MMP-1 alone in a sample of wound fluid before treatment with oxidised cellulose is not a useful indicator of the likelihood that the wound would respond well to said treatment.

Reference Example 4

Concentration of MMP-1+MMP-9

The combined amount of MMP-1 and MMP-9 in wound samples of the patients was determined according to the method of Example 2, above. The data are presented as a box plot in FIG. 21 and clearly show that before treatment with oxidised cellulose commenced (i.e. at week 0), there was no significant difference between the combined sum of MMP-1 and MMP-9 concentration in patients identified as responders and those identified as non-responders (responders and non-responders are as defined in Example 4). Accordingly, the combined amount of MMP-1 and MMP-9 in a sample of wound fluid before treatment with oxidised cellulose is not a useful indicator of the likelihood that the wound would respond well to said treatment.

Reference Example 5

Concentration of the Inflammatory Cytokine Tumor Necrosis Factor Receptor II (TNFR-II)

The amount of TNFR-II in wound samples of the patients was determined by protein microarray substantially according to the method of Example 2, above. The data are presented as a box plot in FIG. 22 and clearly show that before treatment with oxidised cellulose commenced (i.e. at week 0), there was no significant difference between the TNFR-II concentration in patients identified as responders and those identified as non-responders (responders and non-responders are as defined in Example 5). Accordingly, the amount of TNFR-II in a sample of wound fluid before treatment with oxidised cellulose is not a useful indicator of the likelihood that the wound would respond well to said treatment.

Reference Example 6

Concentration of the Growth Factor Vascular Endothelial Growth Factor (VEGF)

The amount of VEGF in wound samples of the patients was determined according to a method analogous to that described above in Example 2. The data are presented as a box plot in FIG. 23 and clearly show that before treatment with oxidised cellulose commenced (i.e. at week 0), there was no significant difference between the VEGF concentration in patients identified as responders and those identified as non-responders (responders and non-responders are as defined in Example 5). Accordingly, the amount of VEGF in a sample of wound fluid before treatment with oxidised cellulose is not a useful indicator of the likelihood that the wound would respond well to said treatment.

CONCLUSION

The present inventors have discovered that non-healing wounds can be distinguished from healing wounds by measuring both human neutrophil elastase (hNE) activity and the activity of at least one matrix metalloproteinase (MMP) in a sample of the wound fluid, and comparing these measured values with threshold values indicative of non-healing wounds. Suitably, non-healing wounds may be distinguished from healing wounds by determining a weighted average (weighted sum) of the levels of human neutrophil elastase (hNE) and at least one matrix metalloproteinases (MMP), or, more suitably two or more matrix metalloproteinases (MMP); and assigning said wound to a non-healing category if said weighted average exceeds a threshold level The measurement of both analyte types compensates for inter-patient variations in the individual analytes and thereby reduces false negative results. The selection of a sufficiently high threshold reduces false positive results. Overall, at least 80% or 90% of the wounds giving a positive result in this test are found to be non-healing.

Accordingly, from these data the inventors have also found that the measurement of total protein in a sample of wound fluid, or the measurement of individual marker analytes in samples of wound fluid, such as the measurement of individual endogenous protease enzymes or inflammatory cytokines has so far been unsuccessful in predicting whether wounds would be responsive to treatment with oxidized cellulose therapy before said treatment has commenced, i.e. at week 0. On the other hand, the present inventors have found, surprisingly, that the combined amount of elastase, MMP-1 and MMP-9 in a sample of a wound fluid, whether before (i.e. week 0) or during (i.e. week 4) treatment with a protease inhibitor dressing, such as an oxidized cellulose dressing, correlates to the likelihood of (and rate of) healing by means of this therapy.

The above embodiments have been described by way of example only. Many other embodiments falling within the scope of the accompanying claims will be apparent to the skilled reader.

We claim:

1. A method of wound prognosis comprising the steps of: determining the combined protease amount of human neutrophil elastase (hNE) and at least one matrix metalloproteinase (MMP) in a sample of wound fluid from a wound, wherein determining comprises allowing the hNE and the at least one MMP to cleave one or more peptide substrates in a single device, whereby a level of cleavage corresponds to the combined protease amount of the hNE and the at least one MMP;

and comparing the combined amount of said proteases with a control standard, and further comprising applying a wound dressing comprising oxidized cellulose to the wound if the combined amount of said proteases is greater than the control standard.

2. A method according to claim 1, wherein the wound dressing comprises a combination of oxidized regenerated cellulose with collagen and/or chitosan in the dry weight ratio of from about 10:1 to about 1:10.

3. A method of detecting whether a weighted average level of human neutrophil elastase (hNE) and at least one matrix metalloproteinase (MMP) in a sample of wound fluid from a wound exceeds a predetermined threshold value for the weighted average, comprising:
    (a) obtaining a sample of wound fluid from a wound; and
    (b) detecting the weighted average level of human neutrophil elastase (hNE) and at least one matrix metalloproteinase (MMP) in the sample of wound fluid by contacting the sample of wound fluid with one or more peptide substrates in a single device, wherein the one or more peptide substrates are cleavable by the hNE and the at least one MMP, whereby the weighted average level of human neutrophil elastase (hNE) and at least one matrix metalloproteinase (MMP) in a sample of wound fluid from a wound is compared to the predetermined threshold value for the weighted average.

4. A method according to claim 3, wherein the at least one matrix metalloproteinase is selected from MMP-1, MMP-2, MMP-8, MMP-9, MMP-12, MMP-13, combinations thereof, and total MMP.

5. A method according to claim 4, wherein the at least one matrix metalloproteinase is selected from MMP-8 and MMP-9.

6. A method according to claim 3, wherein said detecting is performed on a sample of wound fluid that has been removed from a body.

7. A method of claim 3, wherein an amount of protease inhibitors in the sample of wound fluid is not detected.

8. The method of claim 3, wherein the at least one MMP is total protease amount of all MMP types in the sample of wound fluid.

9. The method of claim 3, wherein the one or more peptide substrates are cleaved by both hNE and the at least one MMP.

10. The method of claim 3, wherein the one or more peptide substrates are conjugated to a binding moiety.

11. The method of claim 3, wherein the step of detecting comprises using a lateral flow device for the following steps:
    (a) reacting the sample of wound fluid with the one or more peptide substrates, wherein the one or more peptide substrates are conjugated to a binding moiety;
    (b) mixing the reacted one or more peptide substrates with a chromophore conjugated to a binding partner specific for the one or more peptide substrates; and
    (c) detecting intact binding moiety-peptide substrate: binding partner-chromophore complexes
    wherein the method provides an output signal, which is immediately recognizable or includes further interpretation by reference to a reference standard.

12. The method of claim 3, wherein the one or more peptide substrates are immobilized to a solid support in the device.

13. The method of claim 3, wherein the one or more peptide substrates are conjugated to an indicator moiety or a binding moiety.

14. The method of claim 3, wherein the device is adapted to provide a visual output in the form of a color line on a test strip.

15. The method of claim 3, wherein the one or more peptide substrates comprise SEQ ID NO:12 or SEQ ID NO:7.

\* \* \* \* \*

SEQUENCE LISTING

<160> NUMBER OF SEQ ID NOS: 12

<210> SEQ ID NO 1
<211> LENGTH: 9
<212> TYPE: PRT
<213> ORGANISM: Artificial Sequence

```
<220> FEATURE:
<223> OTHER INFORMATION: synthetic linker

<400> SEQUENCE: 1

Lys Gly Ala Ala Ala Lys Ala Ala Ala
1               5

<210> SEQ ID NO 2
<211> LENGTH: 4
<212> TYPE: PRT
<213> ORGANISM: Artificial Sequence
<220> FEATURE:
<223> OTHER INFORMATION: synthetic linker

<400> SEQUENCE: 2

Ala Ala Pro Val
1

<210> SEQ ID NO 3
<211> LENGTH: 4
<212> TYPE: PRT
<213> ORGANISM: Artificial Sequence
<220> FEATURE:
<223> OTHER INFORMATION: synthetic linker

<400> SEQUENCE: 3

Ala Ala Pro Leu
1

<210> SEQ ID NO 4
<211> LENGTH: 4
<212> TYPE: PRT
<213> ORGANISM: Artificial Sequence
<220> FEATURE:
<223> OTHER INFORMATION: synthetic linker

<400> SEQUENCE: 4

Ala Ala Pro Phe
1

<210> SEQ ID NO 5
<211> LENGTH: 4
<212> TYPE: PRT
<213> ORGANISM: Artificial Sequence
<220> FEATURE:
<223> OTHER INFORMATION: synthetic linker

<400> SEQUENCE: 5

Ala Ala Pro Ala
1

<210> SEQ ID NO 6
<211> LENGTH: 4
<212> TYPE: PRT
<213> ORGANISM: Artificial Sequence
<220> FEATURE:
<223> OTHER INFORMATION: synthetic linker

<400> SEQUENCE: 6

Ala Tyr Leu Val
1

<210> SEQ ID NO 7
<211> LENGTH: 4
<212> TYPE: PRT
<213> ORGANISM: Artificial Sequence
<220> FEATURE:
```

```
<223> OTHER INFORMATION: synthetic linker
<220> FEATURE:
<221> NAME/KEY: MOD_RES
<222> LOCATION: (1)..(1)
<223> OTHER INFORMATION: Xaa = MeOSuccinyl Ala
<220> FEATURE:
<221> NAME/KEY: MOD_RES
<222> LOCATION: (4)..(4)
<223> OTHER INFORMATION: Xaa = Val 7-amino-4-methyl coumarin

<400> SEQUENCE: 7

Xaa Ala Pro Xaa
1

<210> SEQ ID NO 8
<211> LENGTH: 6
<212> TYPE: PRT
<213> ORGANISM: Artificial Sequence
<220> FEATURE:
<223> OTHER INFORMATION: synthetic linker
<220> FEATURE:
<221> NAME/KEY: VARIANT
<222> LOCATION: (3)..(3)
<223> OTHER INFORMATION: Xaa = Any amino acid
<220> FEATURE:
<221> NAME/KEY: VARIANT
<222> LOCATION: (6)..(6)
<223> OTHER INFORMATION: Xaa = Any amino acid

<400> SEQUENCE: 8

Gly Pro Xaa Gly Pro Xaa
1               5

<210> SEQ ID NO 9
<211> LENGTH: 6
<212> TYPE: PRT
<213> ORGANISM: Artificial Sequence
<220> FEATURE:
<223> OTHER INFORMATION: synthetic linker
<220> FEATURE:
<221> NAME/KEY: VARIANT
<222> LOCATION: (6)..(6)
<223> OTHER INFORMATION: Xaa = Any amino acid

<400> SEQUENCE: 9

Gly Pro Leu Gly Pro Xaa
1               5

<210> SEQ ID NO 10
<211> LENGTH: 6
<212> TYPE: PRT
<213> ORGANISM: Artificial Sequence
<220> FEATURE:
<223> OTHER INFORMATION: synthetic linker
<220> FEATURE:
<221> NAME/KEY: VARIANT
<222> LOCATION: (6)..(6)
<223> OTHER INFORMATION: Xaa = Any amino acid

<400> SEQUENCE: 10

Gly Pro Ile Gly Pro Xaa
1               5

<210> SEQ ID NO 11
<211> LENGTH: 5
<212> TYPE: PRT
<213> ORGANISM: Artificial Sequence
<220> FEATURE:
<223> OTHER INFORMATION: synthetic linker
<220> FEATURE:
<221> NAME/KEY: VARIANT
```

```
<222> LOCATION: (5)..(5)
<223> OTHER INFORMATION: Xaa = Any amino acid

<400> SEQUENCE: 11

Ala Pro Gly Leu Xaa
1               5

<210> SEQ ID NO 12
<211> LENGTH: 8
<212> TYPE: PRT
<213> ORGANISM: Artificial Sequence
<220> FEATURE:
<223> OTHER INFORMATION: synthetic linker
<220> FEATURE:
<221> NAME/KEY: MOD_RES
<222> LOCATION: (1)..(1)
<223> OTHER INFORMATION: Xaa = (7-methoxycoumarin-4-yl)acetyl Lys
<220> FEATURE:
<221> NAME/KEY: MUTAGEN
<222> LOCATION: (6)..(6)
<223> OTHER INFORMATION: Xaa = N-3-(2,4-dinitrophenyl)-L-alpha,beta-
      diaminopropionyl

<400> SEQUENCE: 12

Xaa Pro Leu Gly Leu Xaa Ala Arg
1               5
```